(12) United States Patent
Chen

(10) Patent No.: US 7,374,898 B2
(45) Date of Patent: May 20, 2008

(54) PEPTIDE INHIBITORS AGAINST SEPRASE

(75) Inventor: Wen-Tien Chen, Stony Brook, NY (US)

(73) Assignee: The Research Foundation of State University of New York, Albany, NY (US)

( * ) Notice: Subject to any disclaimer, the term of this patent is extended or adjusted under 35 U.S.C. 154(b) by 0 days.

(21) Appl. No.: 11/248,891

(22) Filed: Oct. 11, 2005

(65) Prior Publication Data

US 2006/0172938 A1    Aug. 3, 2006

Related U.S. Application Data

(60) Provisional application No. 60/618,053, filed on Oct. 12, 2004.

(51) Int. Cl.
*A61K 38/10*     (2006.01)
*C12Q 1/44*     (2006.01)

(52) U.S. Cl. .......................................... 435/19; 514/16

(58) Field of Classification Search ..................... None
See application file for complete search history.

(56) References Cited

U.S. PATENT DOCUMENTS

2004/0053829 A1*    3/2004    Pfizenmaier et al. .......... 514/12

OTHER PUBLICATIONS

Kuks PFM et al. Xenopus laevis skin Arg-Xaa-Val-Arg-Gly-endoprotease, 1989, Journal of Biological Chemistry, v264, 14609-14612.*

* cited by examiner

*Primary Examiner*—Anish Gupta
*Assistant Examiner*—Ronald T Niebauer
(74) *Attorney, Agent, or Firm*—Medlen & Carroll, LLP

(57) ABSTRACT

The invention generally relates compositions and methods for the treatment of patients with melanoma and other malignant cancers. The compositions of the present invention are novel peptide sequences that inhibit seprase-mediated cell migration. Said sequences may also be used for diagnostics and library screening protocols.

2 Claims, 6 Drawing Sheets

PEPTIDE INHIBITORS AGAINST SEPRASE

This Application for patent under 35 U.S.C. §111(a) claims priority to Provisional Application Ser. No. 60/618,053 filed Oct. 12, 2004 under 35 U.S.C. 111(b).

This invention was made with funding from the National Institutes of Health, grant number NIH R01CA39077 and R01EB002065. The government has certain rights in this invention.

FIELD OF THE INVENTION

The invention generally relates to novel compounds and methods for the treatment of certain metastatic tumors including but not limited to melanomas and other carcinomas as well as to assays for the qualification and quantitation of tumor invasion, intravasation of cells, and metastasis.

BACKGROUND OF THE INVENTION

Cancer of the skin (non-melanoma and melanoma skin cancers combined) is the most common of all cancers accounting for more than 50% of all cancers. Melanoma accounts for about 4% of skin cancer cases, but causes about 79% of skin cancer deaths. The number of new melanomas diagnosed in the United States is increasing. The American Cancer Society estimates that about 55,100 new melanomas will be diagnosed in the United States during 2004. About 7,910 people in the US are expected to die of melanomas during 2004. Since 1973, the mortality rate for melanoma has increased by 50%. Much of this increase has been in older people, mostly white men. Because of education and early detection, deaths from melanoma are now increasing less rapidly in white men and have leveled off among white women.

Melanoma begins in the melanocytes. Because most of these cells keep on making melanin after becoming cancerous, melanoma tumors are often brown or black. Melanoma most often appears on the trunk of fair-skinned men and on the lower legs of fair-skinned women, but it can appear other places as well. While having dark skin lowers the risk of developing melanoma, it by no means eliminates such risk. Melanoma is almost always curable in its early stages. But it is also likely to spread to other parts of the body. Melanoma is much less common than basal cell and squamous cell skin cancers, but is far more serious.

Currently, treatment options for melanoma include surgery, radiation, chemotherapy, interferon-alpha treatment and vaccine therapy. All of these treatment options are not without problems. For example, surgery is invasive and may leave undetected cancer behind. Radiation and chemotherapy have toxic effects on the patient. Interferon-alpha and vaccine therapies are effective only for a subset of diagnosed patients.

Another prominent cancer of epithelial origin, also noted for its invasiveness, is ovarian epithelial cancer. It is often asymptomatic at its early stages and is only discovered once the disease has progressed to a later stage that manifests as the appearance of destructive growth in primary tumors, and accumulation of ascites in the peritoneal cavity.

Many other cancers generate invasive cells. Non-limiting examples are breast ductal carcinoma (Huang et al., Cancer Res. 64: 2712-2716, 2004; Goodman et al., Clin. Exp. Metastasis 20: 459-470, 2003; Kelly et al., Mod. Pathol. 11: 855-863, 1998; Ariga et al., Int'l J. Cancer 95: 67-72, 2001; Kelly, Drug Resist. Update 8: 51-58, 2005) and gastric (Mori et al., Oncology 67: 411-419, 2004; Okada et al., Oncology 65: 363-370, 2003), colonic (Iwasa et al., Cancer Lett. 227: 229-236, 2005), and cervical carcinoma (Jin et al., Anticancer Res. 23: 3195-3198, 2003). These invasive cells tend to drive the growth and spread of tumors, and are often metastatic.

What is needed are new materials and methods for the treatment of people diagnosed with cancer, including but not limited to melanoma and other carcinomas.

SUMMARY OF THE INVENTION

The invention generally relates to the treatment of patients with cancer (including but not limited to melanoma, breast cancer and other carcinomas) or at risk for cancer. Embodiments of the present invention contemplate novel materials and methods for the treatment of such patients.

In one embodiment, the present invention contemplates peptides and derivatives for the treatment of cancers, including melanoma, that appear to spread by entering the circulation (intravasation) and metastasizing. It is not intended that the present invention be limited by the nature of the agent that alleviates or ameliorates the migration of malignant cells from a primary site, through blood or lymph, to a distant organ. In one embodiment, the present invention contemplates peptides and derivatives for the treatment of tumors that appear to grow and spread due to migration of invasive cells resident in the tumor. It is not intended that the present invention be limited by the nature of the agent that alleviates or ameliorates the migration of invasive cells within a tumor, or at a tumor's invasion front, or into new foci in the tissue that bears the tumor. Such agents can be identified functionally by simply adding them to cell migration assays. Any agent that reduces migration is a candidate. Although the present invention is not limited to any particular mechanism, it is believed the peptides of the present invention work by inhibiting seprase activity, and more specifically the prolyl dipeptidase and gelatinase activities of seprase.

Currently there are no peptide-based therapeutics for the treatment of subjects with melanoma or other malignancies. In one embodiment of the present invention, it is contemplated that the invention comprises the amino acid sequences DMWERVSR [SEQ ID NO.: 1] and DLDYLSKF [SEQ ID NO: 2] and the cyclic versions of these peptides: CDMWERVSRC [SEQ ID NO: 3] and CDLDYLSKFC [SEQ ID NO: 4]. The present invention is not limited to these sequences. One embodiment comprises additional amino acids added to the amino terminus, to the carboxy terminus or to both the amino and carboxy termini of SEQ ID NOS.: 1 and 2. The present invention is not limited to the number of amino acids added to the amino or carboxy termini or the sequence of amino acids added to the amino or carboxy termini. In one embodiment, from one to about 500 amino acids (but more typically 1 to 50) are added to the amino terminus. In another embodiment, from one to about 500 amino acids (but more typically 1 to 50) are added to the carboxy terminus. In yet another embodiment, from one to about 500 amino acids (but more typically 1 to 20) are added to both the amino and carboxy termini. In one embodiment, the number of amino acids added to both the amino and carboxy termini are the same. In another embodiment, the number of amino acids added to the amino and carboxy termini are of a different quantity. In another embodiment, the sequences of the present invention are repeated one or more times (up to about 100 times) in the same polypeptide.

In one embodiment, the present invention also contemplates variations of the SEQ ID NOS: 1-4. For example, sequences based on DXXEXXSR [SEQ ID NO: 5], DXDXXSKX [SEQ JD NO: 6], CDXXEXXSRC [SEQ IID NO: 7] and CDXDXXSKXC [SEQ ID NO: 8] (where any X is any amino acid) are contemplated by the present invention. In one embodiment, cyclic versions of these peptides are contemplated. Furthermore, in yet another embodiment, it is contemplated that the amino acids not designated by X in SEQ ID NOS: 4-8 may be substituted with conservative amino acid substitutions. "Conservative" substitutions are where a substituted amino acid has similar structural or chemical properties. One type of conservative amino acid substitution refers to the interchangeability of residues having similar side chains. For example, glycine, alanine, valine, leucine, and isoleucine is a group of amino acids having aliphatic side chains; serine and threonine is a group of amino acids having aliphatic-hydroxyl side chains; asparagine and glutamine is a group of amino acids having amide-containing side chains; phenylalanine, tyrosine, and tryptophan is a group of amino acids having aromatic side chains; lysine, arginine, and histidine is a group of amino acids having basic side chains; and cysteine and methionine is a group of amino acids having sulfur-containing side chains. Preferred conservative amino acids substitution groups are: valine-leucine-isoleucine, phenylalanine-tyrosine, lysine-arginine, alanine-valine, and asparagine-glutamine.

In yet another embodiment, the amino acids are non-naturally occurring amino acids (non-limiting examples are: Fmoc-(Boc-4-aminomethyl)-L-phenylalanine, Boc-(Fmoc-4-aminomethyl)-L-phenylalanine, Fmoc-(Boc-4-aminomethyl)-D-phenylalanine, Boc-(Fmoc-4-aminomethyl)-D-phenylalanine, Fmoc-4-amino-L-phenylalanine, Boc-4-amino-L-phenylalanine, Fmoc-4-amino-D-phenylalanine, Boc-4-amino-D-phenylalanine, Fmoc-(Boc-4-amino)-L-phenylalanine, Fmoc-(Boc-4-amino)-D-phenylalanine, Fmoc-4-bromo-L-phenylalanine, Boc-4-bromo-L-phenylalanine, Fmoc-4-bromo-D-phenylalanine, Boc-4-bromo-D-phenylalanine, Fmoc-4-bis(2-chloroethyl)amino-L-phenylalanine, Boc-4-bis(2-chloroethyl)amino-L-phenylalanine, Fmoc-2-chloro-L-phenylalanine, Boc-2-chloro-L-phenylalanine, Fmoc-4,5-dehydro-L-leucine and Boc-4,5-dehydro-L-leucine; Fmoc-L-allylglycine, Boc-L-allylglycine dicyclohexylammonium salt, Fmoc-D-allylglycine, Boc-D-allylglycine dicyclohexylammonium salt, Fmoc-DL-methionine methylsulfonium chloride, Boc-DL-methionine methylsulfonium chloride, Fmoc-a-methyl-DL-methionine, Boc-a-methyl-DL-methionine, Fmoc-L-selenomethionine, Boc-L-selenomethionine, Fmoc-DL-selenomethionine and Boc-DL-selenomethionine). Other suitable non-naturally occurring amino acids are known in the art. Still others are commercially available. For example, AnaSpec (San Jose, Calif.) supplies non-naturally occurring amino acids. The exemplary non-naturally occurring amino acids given above have protecting groups (e.g. for ease of peptide synthesis). In another embodiment, non-naturally occurring amino acids do not have protecting groups.

In one embodiment, the present invention contemplates that the peptide sequences of the present invention (other than the cyclic peptides) are terminated with a $CONH_2$ group at the carboxy terminus. Although the present invention is not limited to any particular theory, it is believed that the $CONH_2$ group at the carboxy terminus aids in preventing the degradation of the peptide. In another embodiment, it is contemplated that the sequences of the present invention (other than the cyclic peptides) are terminated with a COOH group at the carboxy terminal. In yet another embodiment, it is contemplated that the sequences of the present invention (other than the cyclic peptides) are terminated with an $NH_2$ group at the N-terminus. In another embodiment, it is contemplated that the peptide sequences of the present invention may additionally comprise carbohydrate groups.

In one embodiment, the present invention contemplates that the peptides of the present invention are protease-resistant. In one embodiment, such protease-resistant peptides are peptides comprising protecting groups. In a preferred embodiment, endoprotease-resistance is achieved using peptides which comprise at least one D-amino acid.

As noted above, the present invention contemplates peptides that are protease-resistant. In one embodiment, such protease-resistant peptides are peptides comprising protecting groups. In a preferred embodiment, the present invention contemplates a peptide containing SEQ ID NOS: 1, 2, 5 or 6 (or a variation as outlined above) that is protected from exoproteinase degradation by N-terminal acetylation ("Ac") and C-terminal amidation (e.g., Ac-DMWERVSR-$NH_2$). The peptide is useful for in vivo administration because of its resistance to proteolysis.

In another embodiment, the present invention also contemplates peptides protected from endoprotease degradation by the substitution of L-amino acids in said peptides with their corresponding D-isomers. It is not intended that the present invention be limited to particular amino acids and particular D-isomers. This embodiment is feasible for all amino acids, except glycine; that is to say, it is feasible for all amino acids that have stereoisomeric forms. By convention, these mirror-image structures are called the D and L forms of the amino acid. These forms cannot be interconverted without breaking a chemical bond. With rare exceptions, only the L forms of amino acids are found in naturally occurring proteins. In one embodiment, the present invention contemplates, for example, DMWER(dV)SR-containing peptides for treatment of melanoma patients. In another embodiment, any of the amino acids may be substituted with the D form of the amino acid. In yet another embodiment of the present invention, more than one amino acid may be substituted with the D form of the amino acid. In still yet another embodiment, any of peptides contemplated by the present invention (e.g., those exemplified by SEQ ID NOS.: 1-8) may have one or more amino acids substituted with the D form of the amino acid.

In one embodiment, the present invention contemplates a composition comprising a polypeptide, said polypeptide having seprase-inhibiting activity and an amino acid sequence that is at least 90% identical to an amino acid sequence selected from the group consisting of SEQ ID NO.: 1, SEQ ID NO.: 2, SEQ ID NO.: 3 or SEQ ID NO.: 4. In a preferred embodiment, said polypeptide comprises a D-amino acid.

In one embodiment, the polypeptide is further modified to resist proteolytic degradation (e.g., upon in vivo delivery). For example, the polypeptide may be modified with protecting groups (e.g., wherein the amino acid sequence of SEQ ID NO: 1 or SEQ ID NO: 2 is N-terminally acetylated and C-terminally amidated).

In one embodiment, the present invention contemplates a compound that inhibits seprase activity, which compound comprises a polypeptide selected from a group consisting of:

| | |
|---|---|
| $Z_1$-DXXEXXSR-$Z_2$ | [SEQ ID NO:16] |
| $Z_1$-DXDXXSKX-$Z_2$ | [SEQ ID NO:17] |
| CDXXEXXSRC | [SEQ ID NO:7] |
| CDXDXXSKXC | [SEQ ID NO:8] | where any X is any amino acid and $Z_1$ and $Z_2$ represent additional amino acids of between 0 (zero) and 50.

The present invention contemplates methods of treating cancer and methods of inhibiting cancer so as to reduce or prevent the spread of the disease, including inhibition of tumor cell migration and intravasation, and reducing, delaying or preventing metastases. In one embodiment, the present invention contemplates a method of treating cancer (e.g., melanoma), comprising: (a) providing a subject diagnosed with cancer (e.g., melanoma) or having symptoms of cancer and, a composition comprising a peptide sequence which inhibits seprase activity; (b) administering said composition to said subject. Administering may be done, in one embodiment, until said symptoms are reduced. In a preferred embodiment, administering is done to reduce tumor growth. In another embodiment, administering is done to inhibit secondary tumor colonization at new foci within a tissue. In another embodiment, administering is done to reduce the number of circulating tumor cells and the formation of metastatic colonies of such cells (e.g., in the lung and liver). While a variety of peptides may be used, in a preferred embodiment, said peptide sequence is selected from a group consisting of SEQ ID NO.: 1, SEQ ID NO.: 2, SEQ ID NO.: 3 or SEQ ID NO.: 4. In another embodiment, said peptide sequence is selected from a group consisting of:

$$Z_1\text{-DXXEXXSR-}Z_2$$

$$Z_1\text{-DXDXXSKX-}Z_2$$

$$\text{CDXXEXXSRC}$$

$$\text{CDXDXXSKXC}$$

where any X is X is any amino acid and $Z_1$ and $Z_2$ represent additional amino acids of between 0 (zero) and 50.

As noted above, the peptide may be further modified (e.g., wherein the amino acid sequence of SEQ ID NO: 1 or SEQ ID NO: 2 is N-terminally acetylated and C-terminally amidated) and may comprise one or more non-naturally occurring amino acids (e.g., at least one D-amino acid).

In one embodiment, the present invention contemplates therapeutics to prevent the migration of malignant cells within a tissue in which malignant cells reside. In one embodiment, the present invention contemplates therapeutics to prevent the migration of malignant cells into the circulation and, thence, to metastases. In another embodiment, the present invention further contemplates that the compounds of the present invention are used in conjunction with other therapeutics. For example, the compounds of the present invention may be administered with agents that relieve symptoms of melanoma or other malignancies (e.g., as discussed above), with agents that relieve pain (e.g., novocaine, morphine, aspirin and other medically recognized pain relief agents), with agents that aid in the administration of the compounds of the present invention (e.g., carriers, elixirs, suspension agents, antimicrobial agents, etc.). In yet another embodiment of the present invention, the therapeutics contemplated by the present invention comprise non-active ingredients (e.g., those approved by the Food and Drug Administration and found to be generally safe and effective). Non-active ingredients are, for example, useful for ease of administration, manufacture and packaging. Non-limiting examples of non-active ingredients include saline solutions, antibiotics, thickeners, thinners, oils, colors, pH adjusting agents, flavors, etc.

BRIEF DESCRIPTION OF THE DRAWINGS

FIG. 6 C&D shows ascites tumor cells freshly seeded on a TRITC-labeled type I collagen film (Reference bar=50 μm). Cells appearing under phase contrast in FIG. 6C show no fluorescence by epifluorescent microscopy in FIG. 6D. FIG. 6 E&F show same field 16 hours later (Reference bar=50 μm). Cells under phase contrast (FIG. 6E) also appear under epifluorescence, demonstrating that ovarian cancer cells digest and ingest the collagen film. Exemplary specific cells indicated by arrows.

DEFINITIONS

Figure 1:
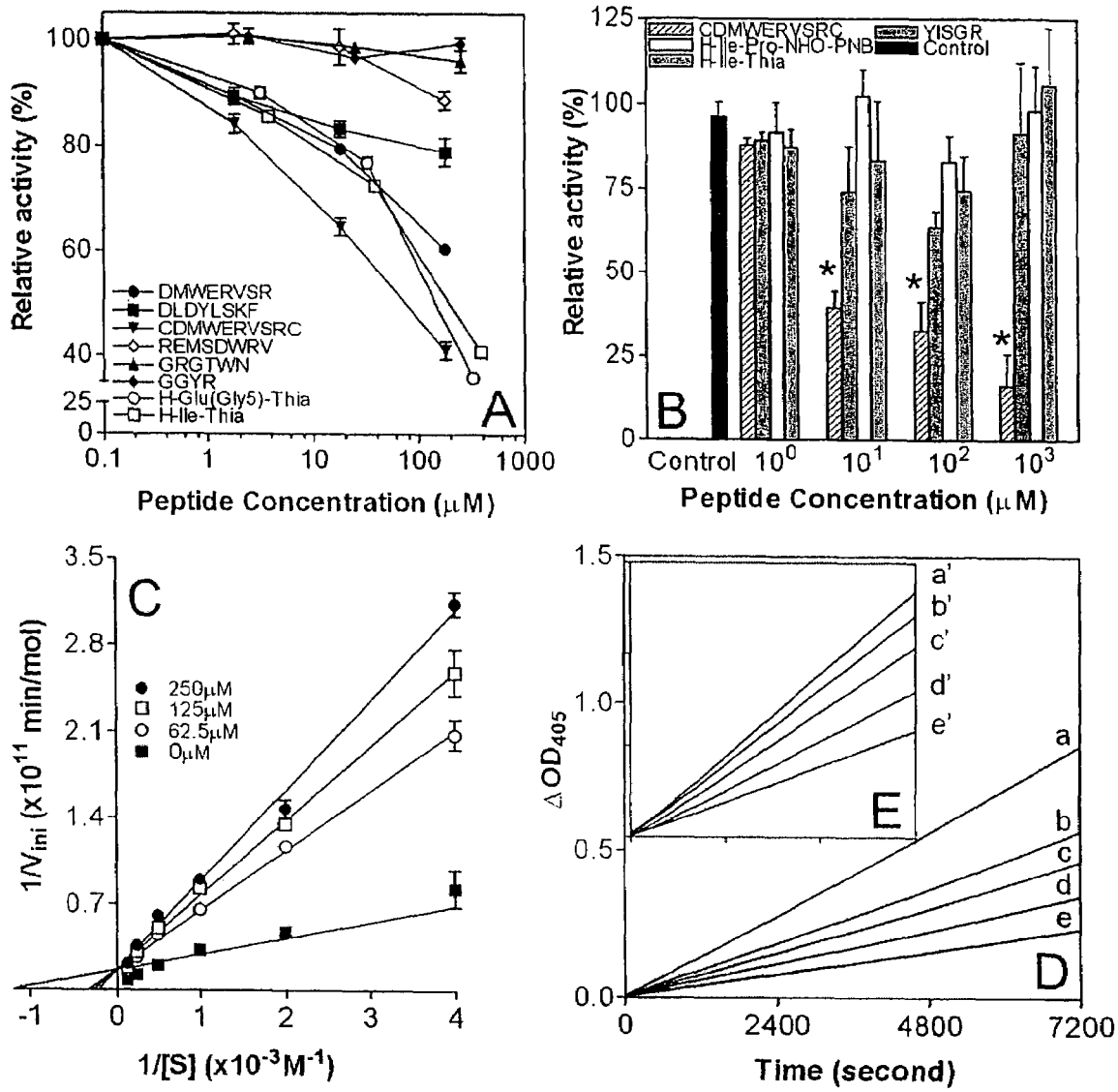
FIG. 1 shows synthetic peptides that block the prolyl dipeptidase and gelatinase activities of seprase. A: Peptide inhibition of the prolyl dipeptidase activity of seprase. B: Peptide inhibition of the gelatinolytic activity of seprase. C: Lineweaver-Burke analysis of the inhibition of seprase prolyl dipeptidase cleavage by CDMWERVSRC [SEQ ID NO: 3]. D: Time progress curves of the seprase prolyl dipeptidase activity in the presence of CDMWERVSRC [SEQ ID NO: 3]. E: Time progress curves of the DPP4 prolyl peptidase activity in the presence of CDMWERVSRC [SEQ ID NO: 3].

The term "melanoma" refers to a tumor arising from the melanocytic system of the skin and other organs. When used alone the term refers to malignant melanoma.

The term "metastatic" refers to a condition (herein, generally, a cancer) or entity (herein, generally, a cancer cell or tumor) capable of transcending its original status or site of origin. "Metastasis" can refer to a metastatic process or to a cancer cell or tumor at a secondary site.

The term "carcinoma" refers generally to a cancer of epithelial origin. As used herein, the term encompasses cancer cells of epithelial origin found outside epithelial tissues.

The term "invasive," as used herein, refers especially to invasive cells or tumors. The term applies to normally invasive cells such as wound-healing fibroblasts and also to cells that migrate abnormally. Although the term is not to be limited by any mechanistic rationale, such cells are thought to migrate by defeating the body's means for keeping them sufficiently "in place" to function normally. Such cells are "invasive" if they migrate abnormally within a tissue or tumor, or escape the tissue, or invade other tissues.

"Ovarian epithelial cancer" herein refers to cancers that originate in the tissue that envelops the ovary.

The term "destructive growth in tumors" encompasses both destruction of normal tissue by a tumor's growth and "destruction" or disruption of the tumor itself.

The term "ascites" refers to fluid in (or withdrawn from) the peritoneal cavity.

The term "intravasation" means the entry of an entity into the vasculature, and refers here especially to the entry of a cancer cell into the blood or lymphatic circulation.

The "invasion front" of a tumor comprises tumor cells growing interfacially with normal tissue or advancing into an unoccupied space such as a body cavity.

The term "tumor invasion" encompasses both invasion by a tumor (e.g., into healthy tissue along an invasion front) and invasion of a tumor (e.g., by a cell migrating aggressively within tumor tissue).

The term "tumor colonization" means the establishment of a tumor in a host tissue. Colonization may take place de novo, by invasion, by metastatic process, or otherwise.

"Anaplasia" refers to any growth of a population of cells that are abnormal structurally or functionally.

The term "activated fibroblast" refers to a connective tissue cell capable of producing collagen, wherein one or more functions of said cell are enhanced or intensified.

The term "prolyl dipeptidase" refers to an enzyme named for its ability to promote cleavage of an N-terminal proline or another imino acid from imidodipeptides, but not limited thereto in its catalytic activities.

The term "DPP-4" refers to one example of a "dipeptidyl peptidase," which refers to any member of a sub-subclass of hydrolase enzymes named for their ability to cleave a dipeptide residue from a free N-terminal end of a peptide or polypeptide, but not limited thereto in their catalytic activities.

The term "gelatinase" refers to an enzyme named for its ability to cleave gelatin (denatured collagens), but not limited thereto in its catalytic activities.

The term "cancer" is a general term for more than 100 diseases that are characterized by the uncontrolled, abnormal growth of cells. Cancer cells can spread locally or can intravasate and spread via the bloodstream and lymphatic system to other parts of the body and form metastases. Cancer cells that spread are called "malignant." The term "malignant" refers to having the properties of anaplasia, penetrance (into the vasculature) and metastasis, said of tumors. The term "tumor" refers to an abnormal mass of tissue that results from excessive cell division that is uncontrolled and progressive. It is also called a neoplasm. Tumors perform no useful body function. They may be either benign (not cancerous) or malignant.

The term "cell migration" refers to the movement of a population of cells from one place to another. Such movement of cells may be normal as in the movement of neural crest cells during morphogenesis or it may be not normal such as with the movement of malignant cancer cells away from primary sites into the vasculature and, thence, into new or secondary sites in other organs.

The term "seprase antagonist" refers to a substance that acts to inhibit (at least partially) the action or activity of seprase.

The term "seprase activity" refers to the natural activity of seprase. While the present invention is not limited to any particular theory, seprase is believed to function by aiding in the dissolution or breakdown of collagen fibers.

The term "seprase inhibiting activity" refers to the ability of a substance (for example, the peptide sequences of the present invention) to lessen seprase activity. The present invention is not limited by the mechanism by which seprase activity is lessened.

The term "seprase-mediated" refers to physiological responses or effects caused at least partly by seprase.

The term "non-naturally occurring amino acid" refers to amino acids that are not normally found in living organisms.

The term "D-amino acid" refers to amino acids that are the dextro-rotatory stereoisomer of an amino acid (as opposed to the levo-rotatory [L-amino acid] stereoisomer). The D-amino acid may be the stereoisomer of a naturally occurring or a non-naturally occurring amino acid.

The term "amino terminus" refers to the end of a peptide or protein that typically ends with an $NH_2$ group.

The term "carboxy terminus" refers to the end of a peptide or protein that typically ends with a COOH group.

The term "protease-resistant" refers to peptides and proteins that are resistant to protease degradation when compared to comparable peptides that are not protease-resistant. A protease is any enzyme that catalyses the splitting of peptide bonds in a protein. A protease may be an endoprotease (splits an interior bond) or an exoprotease (splits a terminal bond). The term "protecting group(s)" refers to molecules that are added to, for example, peptides for the purpose of conferring protease-resistance to the peptide. Examples of protecting groups include, but are not limited to, N-terminal acetyl groups and C-terminal acetate groups.

The term "inhibits" (in the context of, for example, "a peptide sequence which inhibits malignant cell migration") refers to the partial or total inhibition (e.g., of malignant cell migration).

The term "target peptide" is a peptide, protein or glycoprotein to which an amino acid sequence of the present invention is believed to bind and/or interact.

The term "patient" or "subject" is an individual having symptoms of, or at risk for, melanoma or other malignancy. Patients may be human or non-human and may include, for example, animal strains or species used as "model systems" for research purposes.

The term "drug" or "therapeutic" as used herein, refers to any medicinal substance used in humans or other animals. Encompassed within this definition are compound analogs, naturally occurring, synthetic and recombinant pharmaceuticals, hormones, antimicrobials, neurotransmitters, etc.

The term "receptors" refers to structures expressed by cells and which recognize binding molecules (e.g., ligands).

The term "antagonist" refers to molecules or compounds which inhibit or "block" the action or formation of a "native" or "natural" compound (such as seprase). Antagonists may or may not be homologous to these natural compounds in respect to conformation, charge or other characteristics. Thus, antagonists may be recognized by the same or different receptors that are recognized by the natural compound.

The terms "isolated" and the term "purified" in the context of "isolated and purified peptide sequences" refer to the separation of the desired peptide sequence(s) from non-desired peptide sequences and other contaminants (e.g. lipids, carbohydrates, nuclei acids, etc.). The terms "isolated" and "purified" do not necessarily mean isolated and purified to 100% homogeneity, although this is also contemplated. Rather, the terms mean isolated and purified to at least 50% homogeneity. In a preferred embodiment, the peptide sequences are isolated and purified to at lest 75% homogeneity. In a more preferred embodiment, the peptide sequences are isolated and purified to at least 90% homogeneity. After isolation and purification, the peptide sequences can then be mixed with or added to other compounds or molecules.

As used herein, a "pharmaceutical composition" is a composition comprising a sequence or sequences of the present invention and a carrier. The pharmaceutical composition may further comprise a pharmaceutically acceptable excipient. The terms "pharmaceutical composition" and "therapeutic composition" are used herein interchangeably. It is not intended that the pharmaceutical compositions be limited to any particular carrier or excipient.

The terms "protein" and "polypeptide" refer to compounds comprising amino acids joined via peptide bonds and are used interchangeably. A "protein" or "polypeptide" encoded by a gene is not limited to the amino acid sequence encoded by the gene, but includes post-translational modifications of the protein.

Where the term "amino acid sequence" is recited herein to refer to an amino acid sequence of a protein molecule, "amino acid sequence" and like terms, such as "polypeptide" or "protein" are not meant to limit the amino acid sequence to the complete, native amino acid sequence associated with the recited protein molecule. Furthermore, an "amino acid sequence" can be deduced from the nucleic acid sequence encoding the protein.

The phrase "peptide sequences of the present invention" refers to peptide SEQ ID NOS: 1-8 and also any peptide sequences that can be based on SEQ ID NOS: 4-8.

The term "portion" when used in reference to a protein (as in "a portion of a given protein") refers to fragments of that protein. The fragments may range in size from four amino acid residues to the entire amino sequence minus one amino acid. The term "portion" when used in reference to a nucleic acid (as in "a portion of a given nucleic acid") refers to fragments of that nucleic acid. The fragments may range in size from ten bases to the entire nucleic acid sequence minus one base.

In one embodiment of the present invention, the sequences of the present invention may be part of a chimeric polypeptide. The term "chimera" when used in reference to a polypeptide refers to the expression product of two or more coding sequences obtained from different genes, that have been cloned together and that, after translation, act as a single polypeptide sequence. Chimeric polypeptides are also referred to as "hybrid" polypeptides. The coding sequences include those obtained from the same or from different species of organisms. Such synthetic polypeptides may include, for example, targeting sequences. In one embodiment, the chimeric polypeptides of the present invention may also be synthesized on automated peptide synthesizing machines by methods known in the art.

The term "fusion" when used in reference to a polypeptide refers to a chimeric protein containing a protein of interest joined to an exogenous protein fragment (the fusion partner). The fusion partner may serve various functions, including enhancement of solubility of the polypeptide of interest, as well as providing an "affinity tag" to allow purification of the recombinant fusion polypeptide from a host cell or from a supernatant or from both. If desired, the fusion partner may be removed from the protein of interest after or during purification.

The term "homolog" or "homologous" when used in reference to a polypeptide refers to a high degree of sequence identity between two polypeptides, or to a high degree of similarity between the three-dimensional structure or to a high degree of similarity between the active site and the mechanism of action. In a preferred embodiment, a homolog has a greater than 60% sequence identity, and more preferably greater than 75% sequence identity, and still more preferably greater than 90% sequence identity, with a reference sequence.

As applied to polypeptides, the term "substantial identity" means that two peptide sequences, when optimally aligned, such as by the programs GAP or BESTFIT using default gap weights, share at least 80% sequence identity, preferably at least 90% sequence identity, more preferably at least 95% sequence identity or more (e.g., 99% sequence identity). Preferably, residue positions which are not identical differ by conservative amino acid substitutions.

The terms "variant" and "mutant" when used in reference to a polypeptide refer to an amino acid sequence that differs by one or more amino acids from another, usually related polypeptide. The variant may have "conservative" changes, wherein a substituted amino acid has similar structural or chemical properties. One type of conservative amino acid substitution refers to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. More rarely, a variant may have "non-conservative" changes (e.g., replacement of a glycine with a tryptophan). Similar minor variations may also include amino acid deletions or insertions (i.e., additions), or both. Guidance in determining which and how many amino acid residues may be substituted, inserted or deleted without abolishing biological activity may be found using computer programs well known in the art, for example, DNAStar software. Variants can be tested in functional assays. Preferred variants have less than 10%, preferably less than 5% and still more preferably less than 2% changes (whether substitutions, deletions, and so on).

The term "domain" when used in reference to a polypeptide refers to a subsection of the polypeptide which possesses a unique structural and/or functional characteristic; typically, this characteristic is similar across diverse polypeptides. The subsection typically comprises contiguous amino acids, although it may also comprise amino acids which act in concert or which are in close proximity due to folding or other configurations. In one embodiment of the present invention, the sequences of the present invention may be considered domains.

The term "at least one symptom is reduced" means that, after treatment, at least one of any number of symptoms is reduced. The reduction need not be complete. That is, a partial reduction in the symptom is contemplated. Additionally, the symptom need not be reduced permanently. A temporary reduction in at least one symptom is contemplated by the present invention.

The term "subject at risk for cancer" is a person or patient having an increased chance of cancer (relative to the general popultation). Such subjects may, for example, be from families with a history of cancer. Additionally, subjects at risk may be individuals in which there is a genetic history of a particular cancer associated with race, nationality or heritage. In the case of melanoma, subjects are at risk in one embodiment if they have had other types of skin cancers.

DETAILED DESCRIPTION OF THE PREFERRED EMBODIMENTS

In a preferred embodiment, the present invention contemplates novel materials and methods for the treatment of patients with melanoma. Melanoma treatments that are currently employed have limited efficacy especially in people diagnosed with stage II, stage III or stage IV melanoma.

Figure 5:
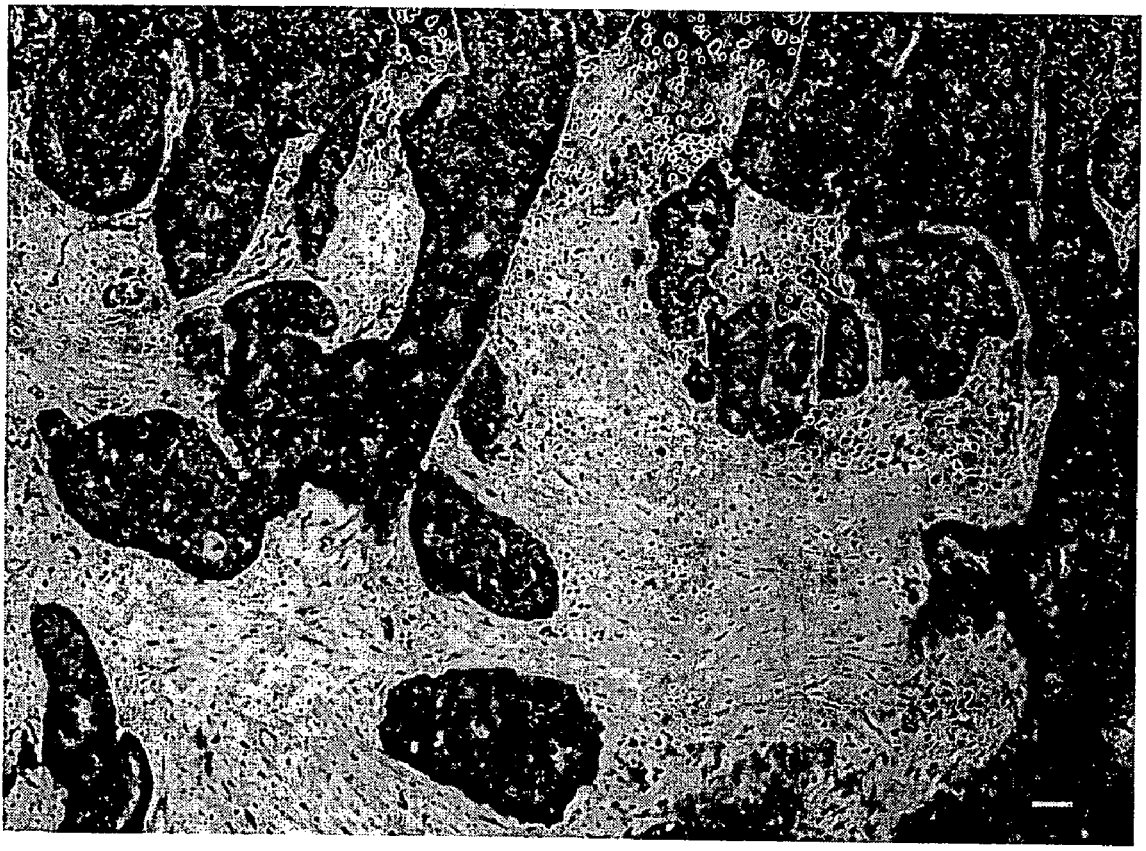
FIG. 5 shows an immuno-histological localization of seprase in the invasion front of a large tumor from a patient with ovarian cancer. Tumor cells and "activated" fibroblasts stain with anti-seprase antibody D28. Reference bar, lower right, is 200 μm.

In another preferred embodiment, the present invention contemplates novel materials and methods for the treatment of patients with ovarian epithelial cancer. Ovarian cancer is often asymptomatic in its early stages and is discovered only after the disease has progressed to a later stage that manifests as the appearance of destructive growth in primary tumors, and accumulation of ascites in the peritoneal cavity. At this stage, seprase is identifiable on tumor cells and activated fibroblasts at the invasion front of human ovarian tumors (FIG. 5). Ovarian tumor cells present in ascites and in peritoneal tumors of human patients, according to a separate DNA micro array study (data not shown) express seprase at a higher level than similar cells in the primary ovarian tumor.

1. Peptide Agents of the Present Invention

In one embodiment, the agents that inhibit seprase comprise a peptide that comprises the sequence DMWERVSR [SEQ ID NO.: 1], DLDYLSKF [SEQ ID NO.: 2], CDMWERVSRC [SEQ ID NO.: 3]or CDLDYLSKFC [SEQ ID NO: 4]and portions and variants thereof (for example, SEQ ID NOS: 5-8 variants). While not limited to any mechanism, it is believed that the peptides of the present invention inhibit seprase activity by binding to seprase molecules and, in doing so, prevent the migration of malignant cancer cells. Seprase is only believed to be expressed in embryonic tissues and non-embryonic adult invasive tumors that become activated to degrade collagenous substrates (Kelly, et al., 1998; Mueller, et al., 1999).

The peptides of the present invention may be synthesized by methods known in the art. For example, peptides may be synthesized by the methods of U.S. Pat. Nos. 6,632,922; 6,649,136; 6,310,180; 4,749,742. Peptides may also be synthesized on automated peptide synthesizing machines (e.g., the Symphony/Multiplex™ automated peptide synthesizer (Protein Technologies, Inc, Tucson, Ariz.) or the Perkin-Elmer (Applied Biosystems, Foster City, Calif.) Model 433A automated peptide synthesizer).

One method of peptide synthesis involves Fmoc (fluorenylmethyloxycarbonyl) chemistry. Fmoc chemistry, as it applies to solid phase peptide synthesis, is well known in the art. All protecting groups that are used to protect the side chain functional groups of individual amino acids are acid labile, while the N-terminal amino function of the amino acid is protected by the Fmoc group which is base labile. Therefore, incorporation of new amino acids is simply a process of treating an Fmoc amino acid that is already attached to a resin with base (e.g., 20% piperidine/DMF) and adding a new Fmoc amino acid activated ester along with the appropriate activator (e.g., N-hydroxy benzotriazole (HOBT)). Within the Fmoc synthetic chemistry scheme there is some flexibility at the coupling stage. Typically, HBTU (1-H-Benzotriazolium)/HOBT is the most widely used coupling reagent used by these automated peptide synthesizers, but other coupling chemistries may be used such as HATU ((N-[Dimethylamino)-1H-1,2,3,-Triazolo[4,5-b]Pyridin-1-YLMethylene]-N-Methylmethanaminium Hexafluophosphate N-Oxide)/HOAT (1-Hydroxy-7-Azabenzotriazole), PyBOP (Benzotriazol-1-yl-oxytripyrrolidino-phosphonium hexafluorophosphate)/HOBT, or OPFP preactivated amino acids/HOBT. Peptides can be synthesized as the free carboxyl or as the C-terminal amide. The N-terminus can be free or acetylated. In addition, the bromoacetylation of the N-terminus and inclusion of norleucine for quantitating the peptide loading onto the carrier protein are routine procedures. Incorporation of unusual amino acid derivatives are only restricted by the availability of the Fmoc activated esters. Both the Symphony and the Perkin Elmer/ABI instruments incorporate the use of HBTU/HOBT for its coupling chemistry. Consequently, each protected amino acid is coupled as the free acid. The first residue may be attached to the HMP (Wang) resin [p-benzyloxybenzyl alcohol resin] using DMAP (4-(Dimethylamino)pyridine) following by a capping step using benzoic anhydride or one can use a variety of preloaded resins.

Peptides synthesized are routinely analyzed by reverse phase HPLC and Mass Spectrometry. HPLC conditions are as follows: * 0.4×25 cm Vydac C18 analytical column * 10-50% Acetonitrile (0.1% TFA)/water * 40 minute linear gradient * Flow rate 1.0 ml/min * UV detector—220 nm * Beckman Diode Array Detector Model 168 * chart speed 0.5 cm/min PAN is currently capable of performing mass spectrometric analysis which is an excellent technique for confirming mass numbers. For example, one such instrument is the Voyager-DE RP Biospectrometry Workstation (AME Bioscience, Norway). This spectrometer is a MALDI-TOF (matrix-assisted laser desorption ionization-time of flight) instrument. It is equipped with delayed extraction (DE) for improved mass accuracy and a reflector (RP) for fragmentation analysis. If the N-terminal amino function of the peptide is free, then N-terminal sequencing of the peptide may be used, if the situation calls for it. For peptides that contain one or more cysteine residues, it is not uncommon to obtain multiple peaks on an HPLC chromatogram due to oxidation of the sulfhydryls. Likewise, methionine can be oxidized to its corresponding sulfoxide which will exhibit itself as an additional peak on the HPLC chromatogram. Other peaks can produced by incomplete deprotection of the Mtr group of Arg, deletion peptides (no capping) or truncated peptides (with capping). Unpurified preparations normally contain 60-95% of the expected product. However, this tends to be peptide-specific.

Under normal synthetic conditions, where the product of interest constitutes the majority of the preparation, yields are of the order of 50%. However, this is highly dependent upon the complexity of the amount of impurities found in the crude peptide as well as of the purification conditions themselves. A typical preparative run can handle 100-150 mg of crude peptide. The preparative column consist of a Millipore 25 mm×10 cm C18 column RCM. Conditions vary and are dependent on the analytical HPLC chromatogram profile. Both isocratic and gradient conditions can be used. Again whether one method is used over the other, is dependent on the analytical HPLC chromatogram profile.

2. Seprase Binding Agents and Antagonists

A. Designing Mimetics

Compounds mimicking the necessary conformation for recognition and binding to the seprase are contemplated as within the scope of this invention. For example, in one embodiment, mimetics of SEQ ID NOS: 1-8 and all of the peptides of the present invention are contemplated. A variety of designs for such mimetics are possible. U.S. Pat. No. 5,192,746 to Lobl, et al, U.S. Pat. No. 5,169,862 to Burke, Jr., et al, U.S. Pat. No. 5,539,085 to Bischoff, et al, U.S. Pat. No. 5,576,423 to Aversa, et al, U.S. Pat. No. 5,051,448 to Shashoua, and U.S. Pat. No. 5,559,103 to Gaeta, et al, all hereby incorporated by reference, describe multiple methods for creating such compounds.

Synthesis of nonpeptide compounds that mimic peptide sequences is also known in the art. Eldred, et al, (*J. Med. Chem.* 37:3882 (1994)) describe nonpeptide antagonists that mimic the Arg-Gly-Asp sequence. Likewise, Ku, et al, (*J. Med. Chem.* 38:9 (1995)) give further elucidation of the synthesis of a series of such compounds. Such nonpeptide compounds that mimic, for example, DMWERVSR [SEQ ID NO: 1] peptides (or, of any one or more of the polypeptides of the present invention) are specifically contemplated by the present invention.

The present invention also contemplates synthetic mimicking compounds that are multimeric compounds that repeat the relevant peptide sequence. In one embodiment of the present invention, it is contemplated that the relevant peptide sequences are SEQ ID NOS.: 1-4; in another embodiment, the relevant peptide sequences are given with SEQ ID NOS: 5-8. As is known in the art, peptides can be synthesized by linking an amino group to a carboxyl group that has been activated by reaction with a coupling agent, such as dicyclohexylcarbodiimide (DCC). The attack of a free amino group on the activated carboxyl leads to the formation of a peptide bond and the release of dicyclohexylurea. It can be necessary to protect potentially reactive groups other than the amino and carboxyl groups intended to react. For example, the a-amino group of the component containing the activated carboxyl group can be blocked with a tertbutyloxycarbonyl group. This protecting group can be subsequently removed by exposing the peptide to dilute acid, which leaves peptide bonds intact. With this method, peptides can be readily synthesized by a solid phase method by adding amino acids stepwise to a growing peptide chain that is linked to an insoluble matrix, such as polystyrene beads. The carboxyl-terminal amino acid (with an amino protecting group) of the desired peptide sequence is first anchored to the polystyrene beads. The protecting group of the amino acid is then removed. The next amino acid (with the protecting group) is added with the coupling agent. This is followed by a washing cycle. The cycle is repeated as necessary. In one embodiment, the mimetics of the present invention are peptides having sequence homology to SEQ ID NOS: 1-4 (or, to any one or more of the polypeptides sequences of the present invention).

One common methodology for evaluating sequence homology, and more importantly statistically significant similarities, is to use a Monte Carlo analysis using an algorithm written by Lipman and Pearson to obtain a Z value. According to this analysis, a Z value greater than 6 indicates probable significance, and a Z value greater than 10 is considered to be statistically significant. W. R. Pearson and D. J. Lipman, Proc. Natl. Acad. Sci. (USA), 85:2444-2448 (1988); D. J. Lipman and W. R. Pearson, Science, 227:1435-1441 (1985). In the present invention, synthetic polypeptides useful in the treatment of patients with melanoma or other malignancies are those peptides with statistically significant sequence homology and similarity (Z value of Lipman and Pearson algorithm in Monte Carlo analysis exceeding 6).

The present invention also contemplates peptide sequence derivatives of SEQ ID NOS: 1-4 (or any one or more of the polypeptides sequences of the present invention) identified by means of an amino acid pairing technique. Root-Bernstein, R. S., "Amino Acid Pairing" *J. Theor. Biol.* 94:885-859 (1982); and Stefanowicz et al., "The new hypothesis on amino acid complementarily and its experimental proof" *Letters in Peptide Science* 5:329-331 (1998). To identify peptide sequence derivates useful in the present invention, the methodology is adapted to identify sequences that are in some wise complementary to seprase, but that specifically inhibit seprase activity without, at the same time, themselves potentiating the migration of cells.

B. Administering Therapeutics

It is contemplated that the antagonists of seprase activity (e.g., the sequences of the present invention such as, but not limited to, SEQ ID NOS: 1-4), can be administered systemically or locally to inhibit melanoma and malignant cell migration in patients. They can be administered by any route including directly into a tumor mass, intravenously, intrathecally, intraperitoneally as well as orally. It is contemplated that the polypeptide agents of the present invention can be administered alone or in combination with other known drugs to treat melanoma and malignancies, as discussed above.

Where combinations are contemplated, it is not intended that the present invention be limited by the particular nature of the combination. The present invention contemplates combinations as simple mixtures as well as chemical hybrids. An example of the latter is where the seprase antagonist is covalently linked to a targeting carrier or to an active pharmaceutical. Covalent binding can be accomplished by any one of many commercially available crosslinking compounds.

It is not intended that the present invention be limited by the particular nature of the therapeutic preparation. For example, such compositions can be provided together with physiologically tolerable liquid, gel or solid carriers, diluents, adjuvants and excipients.

These therapeutic preparations can be administered to mammals for veterinary use, such as with domestic animals, and clinical use in humans in a manner similar to other therapeutic agents. In general, the dosage required for therapeutic efficacy will vary according to the type of use and mode of administration, as well as the particularized requirements of individual hosts.

Such compositions are typically prepared as liquid solutions or suspensions, or in solid forms. Oral formulations usually will include such normally employed additives as binders, fillers, carriers, preservatives, stabilizing agents, emulsifiers, buffers and excipients as, for example, pharmaceutical grades of mannitol, lactose, starch, magnesium stearate, sodium saccharin, cellulose, magnesium carbonate, and the like. These compositions take the form of solutions, suspensions, tablets, pills, capsules, sustained release formulations, or powders, and typically contain 0.1%-95% of active ingredient, preferably 0.2%-70%.

The compositions are also prepared as injectables, either as liquid solutions or suspensions; solid forms suitable for solution in, or suspension in, liquid prior to injection may also be prepared.

The seprase antagonists of the present invention are often mixed with diluents or excipients which are physiological tolerable and compatible. Suitable diluents and excipients are, for example, water, saline, dextrose, glycerol, or the like, and combinations thereof. In addition, if desired the compositions may contain minor amounts of auxiliary substances such as wetting or emulsifying agents, stabilizing or pH buffering agents.

Additional formulations which are suitable for other modes of administration, such as topical administration, include salves, tinctures, creams, lotions, and, in some cases, suppositories. For salves and creams, traditional binders, carriers and excipients may include, for example, polyalkylene glycols or triglycerides.

C. Diagnostics

The polypeptide sequences of the present invention, in certain embodiments, are contemplated for use in diagnostic assays. For example, in one embodiment, the sequences of the present invention are contemplated for use in identifying cancers with seprase activity. In another embodiment, they are used as positive controls in screening assays for agents that identify inhibitors of seprase activity. Comparing cell signal pathway activation in cells treated with the sequences of the present invention versus cells treated with other agents or no agents will aid in the determination of cell signal pathways used in cell migration involving seprase. Such knowledge will be instrumental in determining the molecular basis for malignant cell migration. Such knowledge will also be useful in finding other treatments for melanoma and other malignancies.

EXPERIMENTAL

The following examples serve to illustrate certain preferred embodiments and aspects of the present invention and are not to be construed as limiting the scope thereof.

In the experimental disclosure which follows, the following abbreviations apply: M (Molar); μM (micromolar); mM (millimolar); N (Normal); mol (moles); mmol (millimoles); μmol (micromoles); nmol (nanomoles); g (grams); mg (milligrams); μg (micrograms); L (liters); ml (milliliters); μl (microliters); cm (centimeters); mm (millimeters); μm (micrometers); nm (nanometers); ° C. (degrees Centigrade); MW (molecular weight); h (hours); d(days); sec (seconds); ms (milliseconds); TBS (tris buffered saline); HRP (horse radish peroxidase).

The human malignant amelanotic melanoma cell line LOX was supplied by Dr. O. Fodstad, Institute for Cancer Research, The Norwegian Radium Hospital, Oslo, Norway. Hybridoma cell lines that secreted antibodies D8 (directed against seprase) have been previously described (Pineiro-Sanchez, et al., 1997). The matrix metalloproteinase inhibitor CT-1746 (C19H28ClN3O4, MW 398, Ki=122 nM) was provided by CellTech Ltd. (Slough, United Kingdom). Rabbit anti-rat IgG was purchased from Rockland (Gilbertsville, Pa.); anti-M13 HRP conjugates and 2,2'-azino-di-(3-ethylbenziazoline sulfonate-6) (ABTS) were from Amersham pharmacia Biotech (Piscataway, N.J.); Glycine-Proline p-nitroanilide (p-Toluenesulfonate salt, Gly-Pro-pNA) was from Sigma (St. Louis, Mo.); EnzChek Gelatinase/Collagenase assay kit, Live/Dead viability/cytotoxicity kit, Vybrant Apoptosis Assay Kit #4, and BODIPY FL C5 from Molecular Probes (Eugene, Oreg.); Tetramethyl rhodamine isothiocyanate (TRITC) was from Research Organics, Inc (Cleveland, Ohio). Peptides were synthesized by Biosynthesis Incorporated (Lewisville, Tex.). Phage display peptide libraries (6-15 mer) and bacteria strain K91 were supplied by Dr. George P. Smith (University of Missouri).

EXAMPLE 1

Isolation of peptides that bind seprase. Native seprase, which was isolated from LOX cells grown on type I collagen films according to previously described procedures (Ghersi, et al., 2002; Mueller, et al., 1999; Pineiro-Sanchez, et al., 1997), was used as bait for screening peptides targeted to seprase. Immediately before screening, the wheat germ agglutinin (WGA)-enriched seprase fraction was further immuno-captured on a solid support using mAb D8 against seprase followed by washing with RIPA buffer containing 0.1% sodium dodecyl sulfate (SDS) to remove potential seprase-associated proteins and to make accessible seprase binding sites (Ghersi, et al., 2002; Mueller, et al., 1999; Pineiro-Sanchez, et al., 1997). Anti-seprase mAb D8 (50 μg/ml) was coated on a sterilized tissue culture dish at room temperature for 2 h. Following blocking using 1% BSA in PBS, seprase (10 μg/ml) was added and incubated for 2 h. Phage (containing >$10^{10}$ virions in 1.0 ml TBS) was added and incubated for 1 h. The dish was extensively washed with TBST (TBS with 0.05% tween-20) for 15 times. Fresh K91 bacteria culture ($OD^{600}$ 0.3-0.5; 2 ml) was added and incubated for 20 min. To amplify selected phage, bacteria were collected and transferred to 100 ml of LB medium and cultured overnight. After 4 rounds of biopanning and 6 pre-adsorption rounds, a "negative absorption" step consisting of passing the phage pool over a solid support that had not been previously been primed with seprase, were carried out to eliminate phage that bind to anti-seprase mAb or to background blocking proteins. Selected clones were amplified overnight and their binding to seprase was verified by an ELISA, in which phage were incubated for 1 h in seprase coated microtiter wells (control wells without seprase), and labeled with mouse anti-M13 HRP conjugated mAb. Seprase-binding phage were determined by green color developed using HRP substrate ABTS and measured at 405 nm. We defined the positive clone as $OD^{405}$ (experiment)/$OD^{405}$ (control)>3.0. Positive clones were subjected to DNA sequencing.

We selected potential peptide inhibitors of seprase from a collection of degenerate 6-15 peptides displayed on filamentous phage provided by Dr. George Smith (Matthews, et al., 2002). Promising results were obtained from 8-mer phage libraries. After 4 rounds of biopanning and 6 rounds of pre-adsorption (see Experimental Protocol), pronounced enrichment in phage binding to purified seprase in relation to bovine serum albumin (BSA; control protein) was detected. The nucleotide sequences of over 70 positive clones were determined, and consensus sequences built from the positive clones defined two peptides, DMWERVSR [SEQ ID NO: 1]and DLDYLSKF [SEQ ID NO: 2]. Interestingly, two sequences shared a similar motif, D-E (D) - SR(K), in which two acidic residues were located at the N-terminal and a serine and a basic residue at the C-terminal.

EXAMPLE 2

Peptide inhibitors targeting seprase. Peptides were synthesized corresponding to the degenerated sequences derived from positive phage. Two peptides, DMWERVSR [SEQ ID NO: 1] and DLDYLSKLF [SEQ ID NO: 2], were potent inhibitors of seprase (FIG. 1). A cyclic peptide CDMWERVSRC [SEQ ID NO: 3] and a scramble peptide REMSDWRV [SEQ ID NO: 10] derived from DMWERVSR were then synthesized and tested in two independent proteolytic assays. FIG. 1 shows synthetic peptides that block the prolyl dipeptidase and gelatinase activities of seprase. FIG. 1 A shows peptide inhibition of the prolyl dipeptidase activity of seprase. FIG. 1B shows peptide inhibition of the gelatinolytic activity of seprase.

The assays were performed essentially as follows. DQ-gelatin (25 μg/ml) was added to react with seprase in the presence of different concentrations of peptides at 37° C. for 16 hours. Gelatinolytic activity of seprase was detected by the increase of fluorescent intensity at 485 nm (excitation)/538 nm (emission). CDMWERVSRC [SEQ ID NO: 3] shows dose-dependent inhibition, but YISGR [SEQ ID NO: 9] and two DPP4 inhibitors (H-Ile-Pro-NHO-PNB and H-Ile-Thia) do not. Each histogram bar represents mean±S.E.M (n=3). *P<0.001, t-test. C: Lineweaver-Burke analysis of the inhibition of seprase prolyl dipeptidase cleavage by CDMWERVSRC [SEQ ID NO: 3]. Seprase was pre-incubated in PBS, pH 7.4 with different concentrations of CDMWERVSRC [SEQ ID NO: 3] before adding different concentrations of Gly-Pro-pNA. The rate of hydrolysis was monitored for 1 h. Each data point represents mean±S.E.M (n=4). D: Time progress curves of the seprase prolyl dipeptidase activity in the presence of CDMWERVSRC [SEQ ID NO: 3]. Seprase was reacted with 0 (a), 5.0 (b), 10.0 (c), 30.0 (d) and 60.0 (e) mM of CDMWERVSRC [SEQ ID NO: 3] in PBS, pH7.4 at 37° C. in the presence of 8.0 mM Gly-Pro-pNA. The reaction was initiated by the addition of enzyme. E: Time progress curves of the DPP4 prolyl peptidase activity in the presence of CDMWERVSRC [SEQ ID NO: 3]. DPP4 was reacted with 0 (a'), 32 (b'), 125 (c'), 250 (d') and 500 (e') mM CDMWERVSRC [SEQ ID NO: 3] in PBS, pH 7.4 at 37° C. in the presence of 8.0 mM Gly-Pro-pNA. The reaction was initiated by the addition of enzyme.

The cyclic peptide CDMWERVSRC [SEQ ID NO: 3] and the scramble peptide REMSDWRV [SEQ ID NO: 10] derived from DMWERVSR [SEQ ID NO: 1] were tested in two independent proteolytic assays, i.e., using Gly-Pro-pNA and fluorescent DQ-gelatin as substrates (as described above). In a prolyl dipeptidase assay using the Gly-Pro-pNA substrate (FIG. 1A), DMWERVSR [SEQ ID NO: 1] was more active than DLDYLSKF [SEQ ID NO: 2] in inhibiting seprase. In this assay, prolyl dipeptidase substrate Gly-Pro-pNA (2 mM) was added to react with seprase in the presence of different concentrations of peptides and the absorbance was read at 405 nm. Two peptides (DMWERVSR [SEQ ID NO:1] and DLDYLSKF [SEQ ID NO:2]), a circular peptide CDMWERVSRC [SEQ ID NO:3] (derived from DMWERVSR [SEQ ID NO:11]) and two DPP4 inhibitors (H-Glu (Gly5)-Thia and H-Ile-Thia) inhibit the prolyl dipeptidase activity of seprase.

In parallel, two control peptides, GRGTWN [SEQ ID NO: 11] and GGYR [SEQ ID NO: 12], showed no inhibition, whereas REMSDWRV [SEQ ID NO: 10] (a scrambled sequence of DMWERVSR [SEQ ID NO: 1]) showed a very small inhibitory effect; less than 10% of DMWERVSR [SEQ ID NO: 1] (FIG. 1A). These results indicate that the peptide inhibition of the prolyl peptidase activity of seprase is an attribute of specific peptide sequences. Furthermore, CDMWERVSRC [SEQ ID NO: 3] was more active than DMWERVSR [SEQ ID NO:1 ] and DLDYLSKF [SEQ ID NO:2 ] (FIG. 1A) and inhibited seprase by more than 60% at 100 μM. Each data point represents mean ±S.E.M (n=3). Consistently, other cyclic peptides were found to bind more tightly than their linear sequences as previously shown in MMP peptide inhibitors (Koivunen, et al., 1999).

It was also determined if synthetic peptides targeting seprase could bind seprase-expressing LOX cells but not seprase-negative tumor cells including the human melanoma cell line SKMEL-28. Using ELISA and immunofluorescence, GGAGDMWERVSRG [SEQ ID NO: 13] but not control peptides RKISASEFDRPLR [SEQ ID NO: 14] and GG had strong binding to LOX cells, whereas all three peptides did not bind SKMEL-28 cells, suggesting that the DMWERVSR [SEQ ID NO: 1]-derived peptide is specific for seprase-expressing cells.

The inhibition of the prolyl dipeptidase activity of seprase by CDMWERVSRC [SEQ ID NO: 3] was similar to that of two reported DPP4 competitive inhibitors (FIG. 1A), H-Glu (Gly5)-Thia ($K_{iDPP4}=8\times10^{-8}$ M) and H-Ile-Thia ($K^{iDPP4}=8\times10^{-8}$ M), confirming the results of sequence analyses (Goldstein, et al., 1997; Pineiro-Sanchez, et al., 1997) that seprase and DPP4 share a common catalytic site for cleaving prolyl dipeptide bonds. Prolyl dipeptidase activity of seprase was determined as described in a previous publication (Ghersi, et al., 2002) using Gly-Pro-pNA as substrate. The prolyl peptidase activity was measured by the change of absorbance at 405 nm. One activity unit was defined as the amount of enzyme required releasing 1 nmol of p-nitroniline from Gly-Pro-pNA in one minute. The gelatinolytic activity of seprase was measured using a fluorescein-labeled gelatin (DQ-gelatin, Molecular Probes, Eugene, Oreg.) as substrate. Briefly, seprase was immuno-captured on a 96-well microtiter plate and DQ-gelatin (25 mg/ml) was added and incubated at 37° C. for 16 h. The gelatinolytic activity was detected by the increase of fluorescent intensity at wavelength of 485 (excitation)/538 (emission). One activity unit was defined as the amount of enzyme required to increase fluorescent intensity by one unit in one minute.

We then analyzed the effect of prolyl dipeptide-cleaving inhibitors on the gelatinolytic activity of seprase using a soluble fluorescent DQ-gelatin assay (FIG. 1B). DQ-gelatin (25 µg/ml) was added to react with seprase in the presence of different concentrations of peptides at 37° C. for 16 hours. Gelatinolytic activity of seprase was detected by the increase of fluorescent intensity at 485 nm (excitation)/538 nm (emission). CDMWERVSRC [SEQ ID NO: 3] shows dose-dependent inhibition, but YISGR and two DPP4 inhibitors (H-Ile-Pro-NHO-PNB and H-Ile-Thia) do not. Each histogram bar represents mean±S.E.M (n=3). *P<0.001, t-test. The cyclic peptide CDMWERVSRC [SEQ ID NO: 3], but not other control peptides, inhibited the gelatinolytic activity of seprase (IC50 less than 10 µM). Importantly, the irreversible DPP4 inhibitor H-Ile-Pro-NHO-PNB and H-Ile-Thia did not inhibit the gelatin degradation by seprase (FIG. 1B), suggesting that gelatin-degrading sites are unique for seprase and are resistant to DPP4 inhibitors. It was contemplated that DPP4 and seprase contain the conserved serine protease motif GWSYG [SEQ ID NO: 15] in which the catalytic serine is located in the catalytic triad of S624-D702-H734 (Goldstein, et al., 1997). However, the hydrophobic pocket of the substrate cleft in seprase is different from that of DPP4. Although the inhibitory mechanism of CDMWERVSRC [SEQ ID NO: 3] is still unclear and, indeed, the present invention is neither limited by any mechanism nor is any the knowledge of the mechanism necessary to practice any embodiment of the invention, it is tempting to speculate that the D, E or R residues of CDMWERVSRC [SEQ ID NO: 3] may interact with the catalytic triad and that its tryptophan residue may recognize the hydrophobic pocket of seprase but not DPP4.

To examine the competitive inhibition of seprase, experiments were performed with various concentrations of CDMWERVSRC [SEQ ID NO: 3] and substrate (Gly-Pro-pNA). As shown in the Lineweaver-Burke plot (FIG. 1C), inhibition of the prolyl dipeptidase activity of seprase by CDMWERVSRC [SEQ ID NO: 3] was competitive. When the concentration of CDMWERVSRC [SEQ ID NO: 3] was 62.5 mM, the catalytic Km value increased by 5 times (from 0.7 mM to 3.5 mM). Inhibition of the gelatinolytic activity of seprase by CDMWERVSRC [SEQ ID NO: 3] was dose-dependent (FIG. 1B) and also competitive (data not shown). The time progress curves of seprase activity demonstrated that the interaction of seprase with CDMWERVSRC [SEQ ID NO: 3] followed fast binding kinetics (FIG. 1D), because the shape of the curves in the presence of varying concentrations of CDMWERVSRC [SEQ ID NO: 3] remained the same as in the absence of inhibitor. The Ki value was calculated as $4 \times 10^{-7}$ M based on the result of FIG. 1D. It was then examined whether CDMWERVSRC [SEQ ID NO: 3] effectively inhibited DPP4 that shared a common catalytic motif with seprase (Goldstein, et al., 1997). Inhibition kinetic analysis (Nagase and Salvesen, 2001) showed that the inhibitory activity of CDMWERVSRC [SEQ ID NO: 3] was 100 times more effective against seprase than DPP4 (Ki for DPP4 was $4 \times 10^{-5}$ M), indicating that CDMWERVSRC [SEQ ID NO: 3] is specific against seprase (FIG. 1E). Specifically, H-Ile-Thia effectively blocks the prolyl dipeptidase activity of both seprase and DPP4 with Ki of $1 \times 10^{-7}$ and $8 \times 10^{-8}$ M, respectively. In contrast, CDMWERVSRC [SEQ ID NO: 3] inhibits strongly the prolyl dipeptidase activity of seprase (Ki=$4 \times 10^{-7}$ M) and affects weakly that of DPP4 (Ki=$4 \times 10^{-5}$ M) (FIGS. 1D and 1E).

EXAMPLE 3

Peptide inhibition of the cell invasiveness toward type I collagen films. Next, it was asked whether protease inhibitors were sufficient to affect cellular invasiveness and physiology. We have established an in vitro cell invasion assay using fluorescently labeled type I collagen films prepared according to a recently described protocol (Ghersi, et al., 2002). This is a novel cell invasion assay using fluorescently labeled type I collagen films. TRITC labeled collagen films were made according to a recently reported procedure (Ghersi, et al., 2002). Briefly, labeled collagen solution was mixed with DMEM by 1:4 (v/v), coated as a thin layer in a 16-well chamber slide, and incubated for 1 hour at 37° C. to allow gel formation. LOX cells ($10^3$/well) were loaded and cultured for 16 hours and fixed. The ability of cells to remove and ingest labeled collagen films was observed under a NIKON Eclipse TE300 inverted microscope. Images were taken using a SONY digital photo camera DKC 5000.

Figure 2:
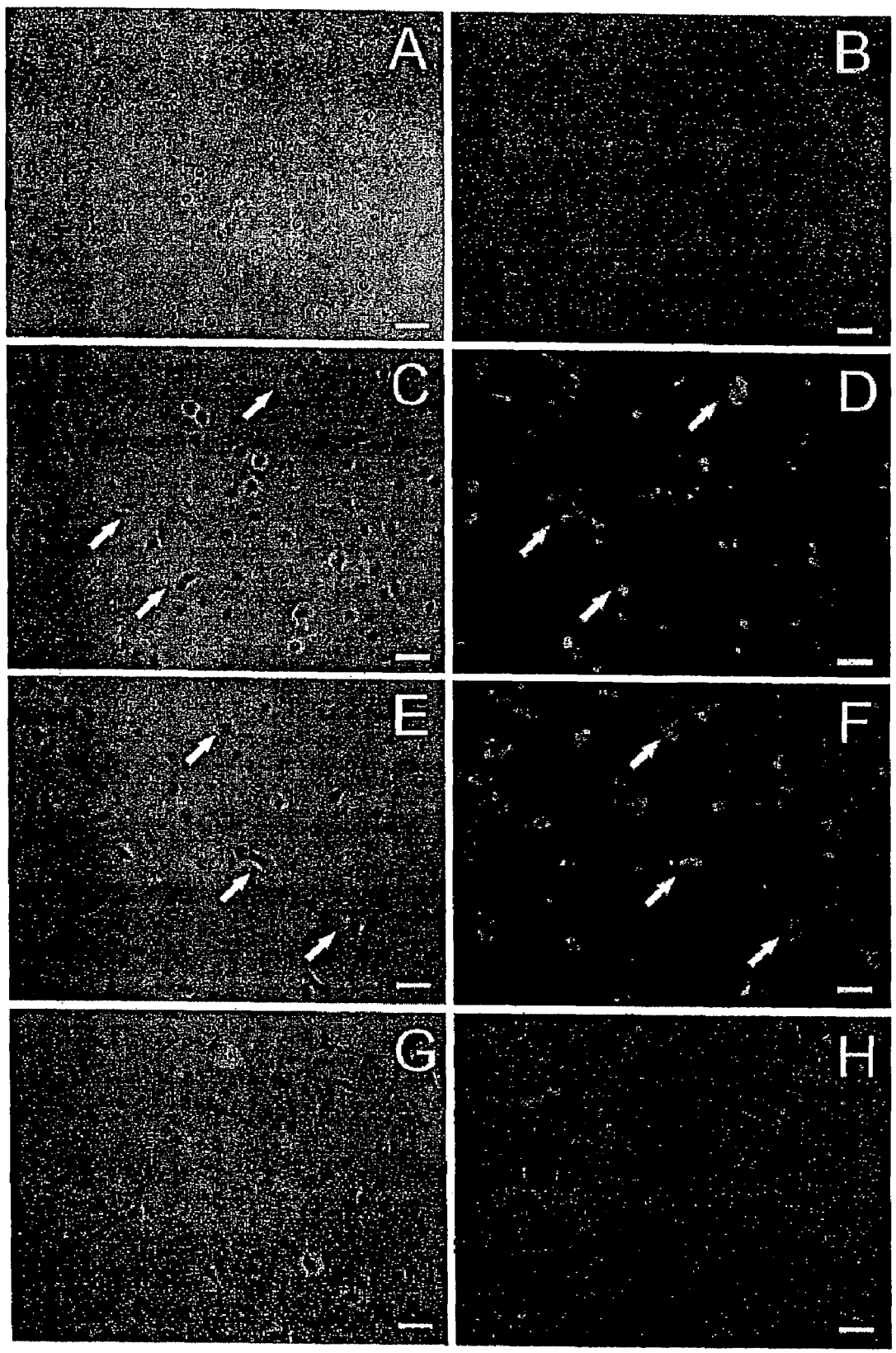
FIG. 2 shows peptide inhibition of cell invasiveness using a collagen invasion assay. A & B: An intact TRITC-labelled type I collagen film underlying freshly seeded LOX cells. Same fields were photographed using phase contrast microscopy for cell morphology (A) and epifluorescence microscopy for the TRITC-type I collagen film (B). Bar, 50 μm. C & D: Partial removal and ingestion of the TRITC-labelled type I collagen film (invasion) by LOX cells. Arrows indicate LOX cells that remove and ingest fluorescently labelled collagen. Bar, 50 μm. E & F: Partial removal and ingestion of the TRITC-labelled type I collagen film (invasion) by LOX cells in the presence of control peptide YISGR (500 μM). Arrows indicate LOX cells that remove and ingest fluorescently labeled collagen. Bar, 50 μm. G & H: Partial inhibition of the TRITC-labelled type I collagen invasion by LOX cells in the presence of CDMWERVSRC [SEQ ID NO: 3] (200 μM). Bar, 50 μm.

FIG. 2 shows that LOX cells adhere to, degrade and ingest collagen films within 18 hours after seeding. Using the fluorescently labeled collagen films, the collagen fragments ingested by invasive cells labeled the cells that retain the invasive phenotype in vitro. Using this assay, the invasiveness of LOX cells is analyzed by the ability of cells to degrade locally collagen films and to ingest collagen fragments (FIG. 2). LOX cells degraded partially the uniform fluorescent collagen film (FIGS. 2A-B) leaving black areas of collagen removal (FIGS. 2C-D). LOX cells also ingested collagen fragments and became labeled with fluorescent spots (FIGS. 2C-D, 2E-F). The fluorescently dark areas on collagen films and spots of collagen ingestion by cells were reduced in cells treated with the cyclic peptide CDMWERVSRC [SEQ ID NO: 3] (FIGS. 2G-H), as compared with these treated with control peptide YISGR [SEQ ID NO: 9] (FIGS. 2E-F).

Figure 3:
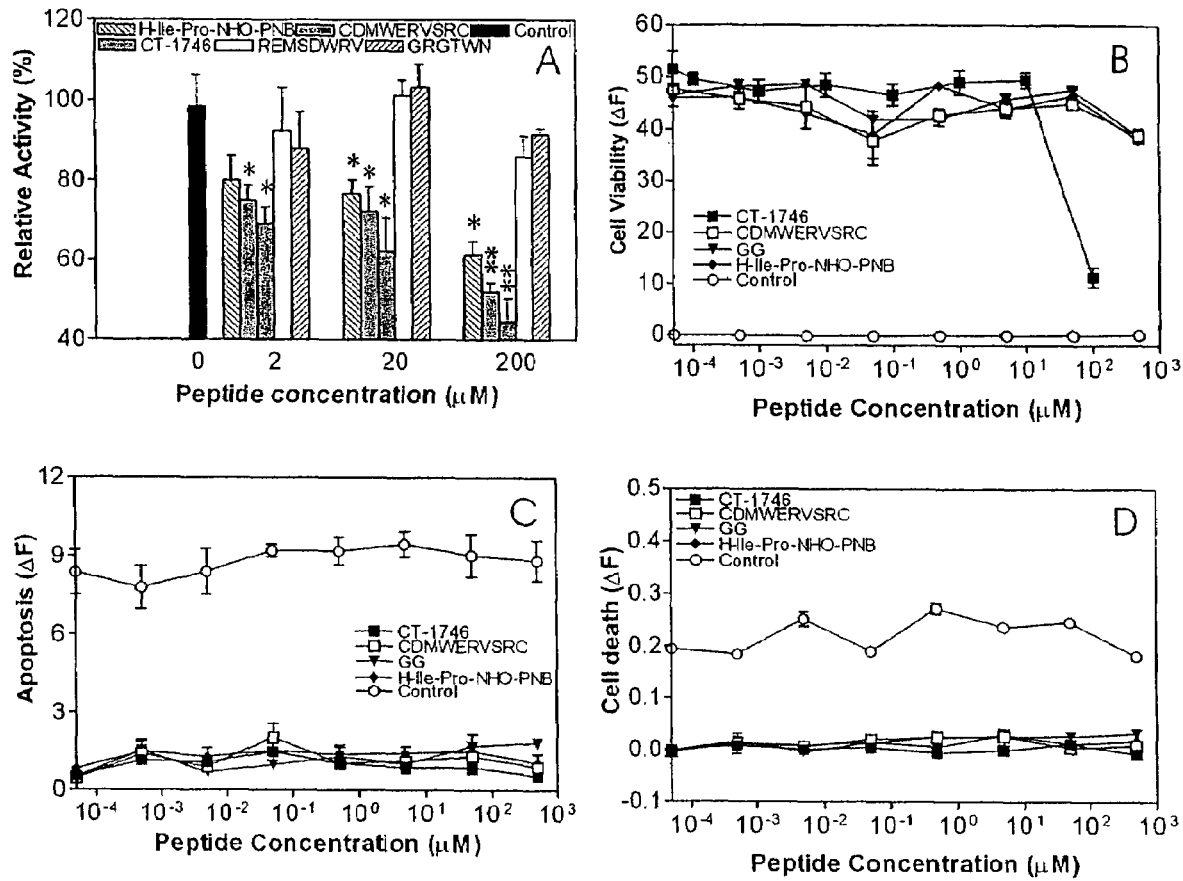
FIG. 3 shows peptide inhibitors that affect the collagen degradation by LOX cells have little effect on cell viability, apoptosis and death. A: Inhibition of the overall collagen degradation by LOX cells. Relative activity was defined by the increase of fluorescent intensity in each well during incubation. Each histogram bar represents mean ±S.E.M (n=3). *$P<0.05$, **$P<0.01$, t-test. B-D: Effects of peptide treatment on cell viability (B), apoptosis (C) and cell death (D). Assays for cell viability (B), apoptosis (C) and cell death (D) are described in detail in Experiment Protocol. Formalin-fixed cells were used as control. Each data point represents mean±S.E.M (n=3).

Conversely, when the overall collagen degradation by the cells was measured in a microtiter plate, we found that CDMWERVSRC [SEQ ID NO: 3], the irreversible DPP4 inhibitor H-Ile-Pro-NHO-PNB and the MMP inhibitor CT-1746 inhibited the overall collagen degradation by LOX cells in a dose dependent manner, whereas control peptides, GRGTWN [SEQ ID NO: 11] and REMSDWRV [SEQ ID NO: 10], did not (FIG. 3A). The assay involves coating 96-well microtiter plates with Bodipy FL C5 labelled type I collagen films. It allows direct measurement of collagen degradation by cells, as the release of fluorescent intensity is in proportion to the degree of collagen degradation. To prepare collagen films, collagen solution mixed with DMEM (1:4 v/v) was coated as a thin layer in each well of a 96-well microtiter plate, and incubated for 1 h at 37° C. to allow gel formation. Labeling of collagen films involved borate buffer, pH 8.3, containing 3 mg of BODIPY FL C5 (Molecular Probes) at 25° C. To determine collagen degradation by cells, LOX cells ($10^4$/well) were seeded in a 96-well microtiter plate pre-coated with Bodipy FL C5 labeled type I collagen, and incubated in the presence of different concentrations of inhibitors at 37° C. for 16 hours. The increase in fluorescence at 485 nm (excitation)/538 nm (emission) is proportional to the ability of cells to degrade fluorescently labeled collagen films. Change in fluorescent intensity was monitored with a fluorescence microtiter plate reader (Molecular Devices, Sunnyvale, Calif.). The IC50 for CDMWERVSRC [SEQ ID NO: 3] on the overall collagen degradation by LOX cells was approximately 200 µM, whereas CT-1746 showed the strongest inhibitory effect and H-Ile-Pro-NHO-pNB was weak (FIG. 3A). The fact that H-Ile-Pro-NHO-pNB partly blocked collagen degradative activity of LOX but not the gelatinolytic activity of pure seprase (FIG. 1B) was probably due to the interaction between serum DPP4 and seprase located on LOX cells (Ghersi, et al., 2002).

In parallel to the assay assessing the overall collagen degradation by LOX cells described above (FIG. 3A), LOX cells grown on collagen films were determined for their physiological responses to peptide or other protease inhibitors in terms of cell viability (FIG. 3B), apoptosis (FIG. 3C) and cell death (FIG. 3D). Cell viability, apoptosis and cell death assays were performed using Molecular Probes (Eugene, Oreg.) Live/Dead Viability/Cytotoxicity kit and Vybrant Apoptosis Assay Kit #4 and followed the manufacturer's instruction. LOX cells ($10^4$/well) were cultured on a type I collagen coated 96-well microtiter plate in the presence of inhibitors at 37° C. overnight. After washing gently with PBS, dyes for the cell viability assay (Calcein Am, 2 mM, only stained live cells) and for the apoptosis assay (YO-PRO [a fluorescent nuclear dye], 0.25 mM, stained apoptotic cells; ethidium homodimer-1, 4 mM, stained dead cells) were added and incubated at 25° C. for 45 min. The fluorescence intensity was read at the wavelength of 485 nm/538 nm or 544 nm/612 nm. In the LIVE/DEAD Viability/Cytotoxicity Assay, high fluorescent intensity indicates high number of viable cells, whereas in the Vybrant Apoptosis Assay, high fluorescent intensity units indicate high number of apoptotic or dead cells.

All inhibitors in concentrations up to 500 mM tested did not show any effect on cell viability except for CT-1746 (FIG. 3B), did not cause apoptosis (FIG. 3C), and did not increase cell death (FIG. 3D). These results indicate that CDMWERVSRC [SEQ ID NO: 3] suppresses the proteolytic activity of seprase to the extent that it completely abrogates seprase function in cell invasiveness toward the extracellular matrix. Moreover, negative results from cell viability, apoptosis and death assays (FIG. 3B-D) suggest that CDMWERVSRC [SEQ ID NO: 3] is not toxic or lethal to cells at doses ranging from $10^4$ to $10^3$ µM, and, therefore, it would be predicted to be less likely to produce side effects in vivo.

EXAMPLE 4

Peptide inhibition of melanoma growth, intravasation and metastasis to lung and liver in SCID or nude mice. We next determined whether CDMWERVSRC [SEQ ID NO: 3] inhibited the growth of human melanoma and metastasis in immuno-deficient mice. GFP-tagged LOX cells, $2 \times 10^5$ cells/mouse, were co-inoculated subcutaneously with peptides into flanks of NCR Nude mice, and followed by daily injections of peptide solutions into sites 2 mm adjacent to tumors. The animal study protocol has been approved by the SUNY Institutional Animal Care and Use Committee. LOX cells were tagged with the green fluorescent protein (GFP) by transfecting with EFGP-C1 vector. Cells were harvested by trypsin/EDTA 48 h after transfection and stable clones were selected in the presence of 400 mg/ml of G418 (Sigma). GFP-tagged LOX cells, $2 \times 10^5$ cells suspended in 100 ml of serum-free DMEM, that were pre-incubated with CDMWERVSRC [SEQ ID NO: 3] (300 µM) or control peptides (500 µM) were injected subcutaneously into flanks of NCR Nude mice (female; Taconic Co., Germantown, N.Y.). In addition, CDMWERVSRC [SEQ ID NO: 3] (300 µM) and control peptides (500 µM) were daily injected into the subcutaneous tissue 2 mm adjacent to tumor sites. Total of 3 mice were used for each experimental or control group. Tumors were measured twice a week. After 28 days, mice were sacrificed by anesthetic overdose. Tissues including primary tumor, lung and liver were removed and examined for GFP tagged melanoma cells and micrometastases by epifluorescence microscopy, followed by enumeration and photography. Melanoma cells in lung and liver were calculated by counting number of GFP-melanoma cells or micrometastases in these tissues freshly excised from animals in a $3 \times 10$ µm$^2$ area in 10 different regions.

The treatment with CDMWERVSRC [SEQ ID NO: 3] delayed the formation of LOX-derived human melanoma (FIG. 4A), whereas control peptide YISGR and medium vehicle did not (FIGS. 4B, 4C). Importantly, seprase-expressing GFP-LOX cells were capable of spontaneously metastasizing to lung and liver within 28 days (FIGS. 4D-K). CDMWERVSRC [SEQ ID NO: 3] significantly delayed formation of lung micrometastases, whereas control peptide YISGR and control vehicle DMEM medium did not (FIGS. 4D,E,F; FIG. 4J). Control groups developed 3 times more lung micrometastases than the experimental group (FIGS. 4D,E,F; FIGS. 4J). Furthermore, CDMWERVSRC [SEQ ID NO: 3] inhibited formation of liver micrometastases, whereas control peptide YISGR and control vehicle DMEM medium did not (FIGS. 4G,H,I; FIG. 4K). Control groups developed 8 times more liver micrometastases than the experimental group (FIGS. 4G,H,I; FIG. 4K).

EXAMPLE 5

Peptide inhibition of tumor invasion, intravasation and metastasis of other solid human cancers in immuno-deficient mice. Next is determined whether the cyclic peptide CDMWERVSRC inhibits the migration of malignant human carcinoma and fibrosarcoma cells within primary tumors, and/or reduces their entry into blood, and/or reduces metastatic formation in the lung and liver. The process of peptide inhibiton is determined by identification of tumor invasion in primary tumor by histology, measurement of intravasation using numbers of lung and liver metastases identified.

EXAMPLE 6

Figure 4:
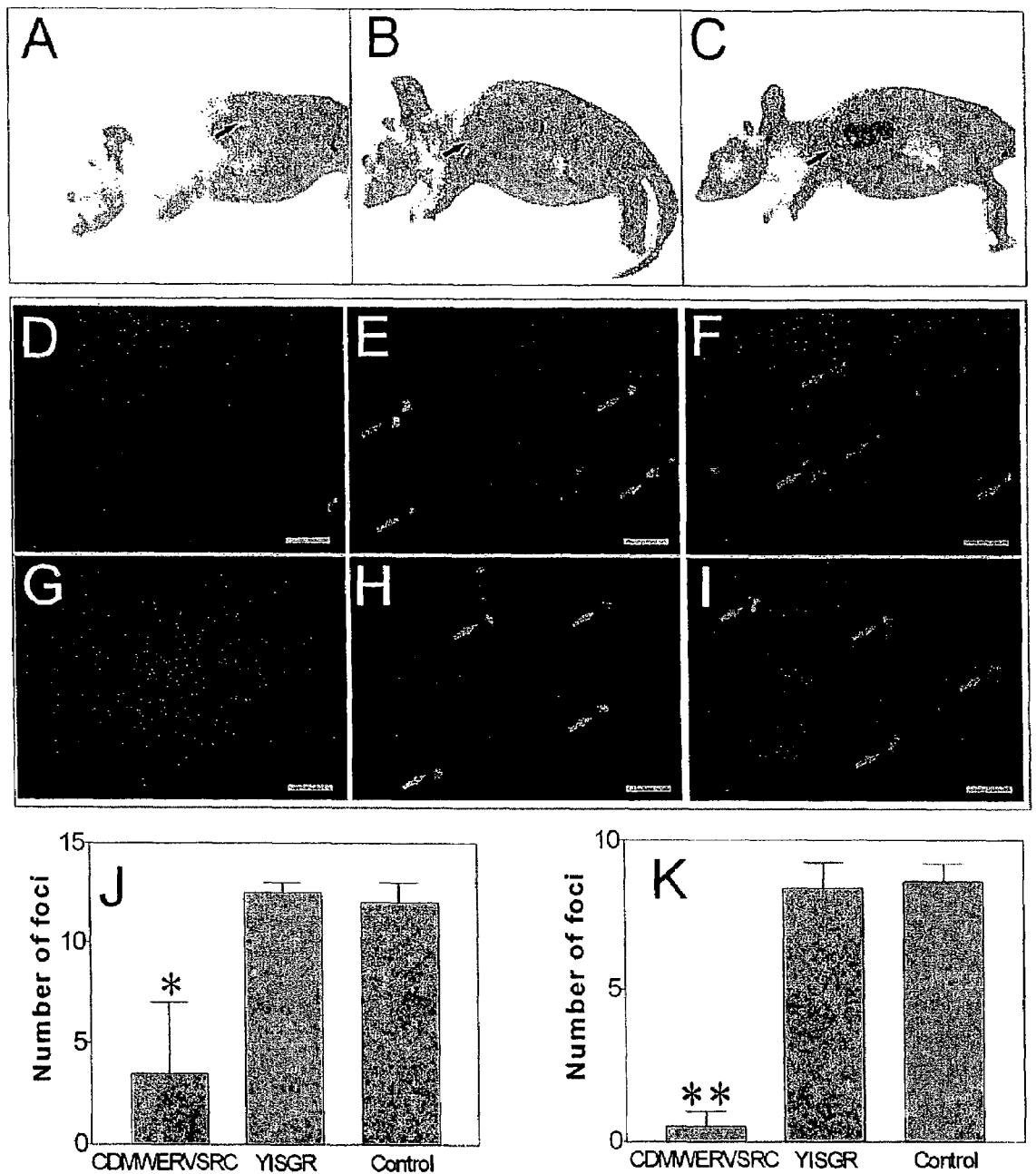
FIG. 4 shows peptide inhibition of melanoma growth and metastasis to lung and liver in nude mice. A-C: Melanoma developed in nude mice that were co-inoculated with GFP-LOX cells and CDMWERVSRC [SEQ ID NO: 3] (A, 300 μM), YISGR [SEQ ID NO: 9] (B, 500 μM) or vehicle only (C). The images were taken 28 days after tumor cell inoculation. D-F: Epifluorescence microscopic identification of lung micrometastases in nude mice that were co-inoculated with GFP-LOX cells and CDMWERVSRC [SEQ ID NO: 3] (D, 300 μM), YISGR [SEQ ID NO: 9] (E, 500 μM) or control vehicle DMEM medium (F). Arrows indicate lung micrometastases. Bar, 50 μm. G-I: Epifluorescence microscopic identification of liver micrometastases in nude mice that were co-inoculated with GFP-LOX cells and CDMWERVSRC [SEQ ID NO: 3] (G, 300 μM), YISGR (H, 500 μM) or control vehicle DMEM medium (I). Arrows indicate liver micrometastases. Bar, 50 μm. J & K: Enumeration of GFP-lung (J) and liver (K) micrometastases in nude mice that were co-inoculated with GFP-LOX cells and CDMWERVSRC [SEQ ID NO: 3] (300 μM), YISGR [SEQ ID NO: 9] (500 μM) or control vehicle DMEM medium. Number of GFP-melanoma cells or micrometastases in lung (J) and liver (K) tissues freshly excised from animals was counted per 3×10⁵ μm² under an epifluorescence microscope. Each data point represents mean ±S.E.M. (n=10). *P=0.04, **P=0.002, t-test.

Using RNA interference technology to determine possible mechanism of seprase inhibiting activity. We have successfully obtained inhibitory peptides by screening peptide substrate phage display libraries that suppressed proteolytic activities of seprase (FIG. 1). These peptides inhibited cell invasiveness (FIGS. 2 & 3) and reduced tumor growth and metastasis (FIG. 4). The CDMWERVSRC [SEQ ID NO: 3] reduced the growth of melanoma and metastasis to lung and liver in nude mice through its target, seprase, on the tumor cell surface. To our knowledge, there are no other proteases or enzymes whose activities direct the tumor invasive and metastatic phenotypes.

Our laboratory has generated evidence using RNA interference technology that suppression of seprase in metastatic human melanoma cells inhibits cell invasiveness toward fibronectin and collagen substrata, and blocks melanoma malignancy resulting in the failure of metastasis at lung and liver. However, wound-induced expression of stromal FAP is transient and occurs during the first three days of healing in gingival wounds (Ghersi, et al., 2002), suggesting that FAP expression is subject to an appropriate regulation (Wesley, et al., 1999). Although the present invention is not limited to any particular mechanism or theory, it is possible that seprase/FAP gene products alone could serve as activators for tumor malignancy to promote tumor cell survival and angiogenesis, and to facilitate metastasis. The dysfunction in cancer may reflect over-production of seprase in malignant tumors and loss of regulation of the increased proteolytic activity necessary for metastasis to progress.

EXAMPLE 7

Figure 6:
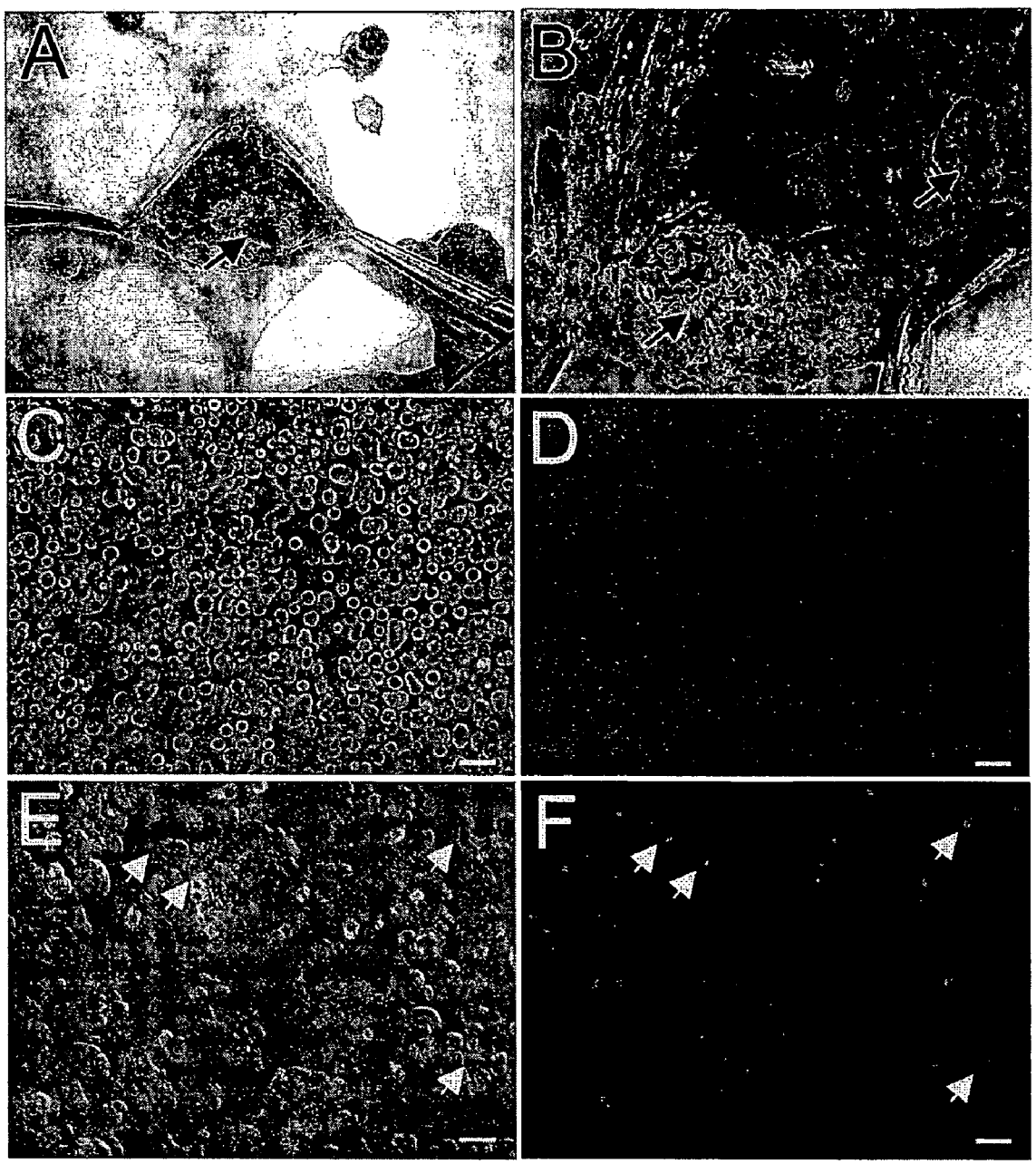
FIG. 6 shows a FOX CHASE SCID™ Beige mouse (C.B-Igh-1bGbmsTac-Prkdcscid-LystbgN7) 8 weeks after intraperitoneal inoculation of human ovarian tumor cells. Ascites evident in FIG. 6A was removed to reveal multimetastatic nodules (at arrows in FIG. 6B).

FIG. 6 shows the development of a human ovarian tumor cell population in ascites and its progression into peritoneal metastases in SCID mice. FOX CHASE™ SCID Beige mice (C.B-Igh-lbGbmsTac-Prkdscid-LystbgN7 that were 4-6 weeks old were used in these studies. These mice not only lack T and B-lymphocytes due to a genetic mutation but they also exhibit a defect in NK cell function. Although the degree to which the immune system of a mouse is compromised does not necessarily reflect its ability to develop tumors or allow for metastasis, in this case the extensively compromised immune status aids in the accumulation of mouse ascites induced by the inoculation of human tumor cells. SCID mice were injected intraperitoneally with $2 \times 10^6$ to $1 \times 10^7$ human ovarian tumor cells isolated from ascites of a patient with metastatic ovarian cancer and incubated for 8 weeks. In this model, DPP4 inhibitor (H-Ile-Pro-NHO-PNB) blocked 50% of growth in ascites and on peritoneum. Equimolecular amounts of seprase-specific CDMWERVSRC [SEQ ID NO:3] inhibited such growth more than 90%. These inhibitors showed no cytotoxicity to mouse and human cells at test concentrations (data not shown), suggesting that the inhibition was due to the loss of seprase and DPP4 activities.

EXAMPLE 8

A human ovarian cancer cell line, SB247, was established from ascites of a patient with metastatic ovarian cancer. Limiting dilutions of cells were aliquoted in 96-well plates and a line was expanded from a single adherent cell. Ideally to more easily detect ascites grown in the in vivo model and later detect tumors in the peritoneal cavity (resulting from the injected cells), the SB247 cell line should be labeled with green fluorescent protein ("GFP"). Because previous attempts to express GFP in thse cells using the pGUS vector had failed, a new vector from Stratagene (pIREShrGFP1a) that contains humanized GFP was used. The new form of GFP alleviated the phenomenon known as GFP toxicity that occurs in certain cells. A hygromycin-resistance gene was added to the plasmid for selection purposes. This new plasmid has successfully created a stable GFP-labeled SB247 cell line. $3 \times 10^6$ GFP-SB247 cells in a 0.5 ml were intraperitoneally injected into female SCID™ Beige mice. This model allows more convenient screening of candidate peptides as inhibitors of seprase.

EXAMPLE 9

The in vivo evidence that CDMWERVSRC [SEQ ID NO:3] inhibits ovarian cancer progression was verified using an in vitro extracellular matrix degradation and ingestion assay as depicted in FIG. 6. It consists of seeding tumor cells on fluorescently labeled type I collagen films and determining the ability of tumor cells to degrade and ingest the fluorescently labeled extracellular matrix. Two inhibitors, H-Ile-Pro-NHO-PNB (DPP4-specific) and the cyclic peptide CDMWERVSRC [SEQ ID NO:3] (seprase-specific) were used. Human ovarian cancer cells isolated from mouse ascites as described in Example 7 were seeded on TRITC-type I collagen films. Within 16 to 24 hours of incubation, the DPP4 inhibitor could block 50% of the degradation and ingestion at 1 mM. The seprase-specific inhibitor was more effective, inhibiting degradation/ingestion by more than 90% at a concentration of 500 μm. Similar results were obtained using human invasive breast carcinoma cell line HS578T, a cell line that over-expresses both seprase and DPP4 (data not shown).

As is evident form the foregoing, the present invention provides novel and non-obvious materials and methods for the treatment of patients with symptoms of melanoma or other malignancy.

What is claimed is:

1. A composition comprising a polypeptide, wherein said polypeptide comprises the amino acid sequence set forth as in the group consisting of SEQ ID NO.: 1, and SEQ ID NO.: 2.

2. A cyclic peptide comprising the amino acid sequence of SEQ ID NO.: 1.

* * * * *

SEQUENCE LISTING

```
<160> NUMBER OF SEQ ID NOS: 17

<210> SEQ ID NO 1
<211> LENGTH: 8
<212> TYPE: PRT
<213> ORGANISM: Artificial Sequence
<220> FEATURE:
<223> OTHER INFORMATION: Synthetic

<400> SEQUENCE: 1

Asp Met Trp Glu Arg Val Ser Arg
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic

<400> SEQUENCE: 2
```

```
Asp Leu Asp Tyr Leu Ser Lys Phe
1               5

<210> SEQ ID NO 3
<211> LENGTH: 10
<212> TYPE: PRT
<213> ORGANISM: Artificial Sequence
<220> FEATURE:
<223> OTHER INFORMATION: Synthetic

<400> SEQUENCE: 3

Cys Asp Met Trp Glu Arg Val Ser Arg Cys
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Synthetic

<400> SEQUENCE: 4

Cys Asp Leu Asp Tyr Leu Ser Lys Phe Cys
1               5                   10

<210> SEQ ID NO 5
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid

<400> SEQUENCE: 5

Asp Xaa Xaa Glu Xaa Xaa Ser Arg
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 6

Asp Xaa Asp Xaa Xaa Ser Lys Xaa
1               5

<210> SEQ ID NO 7
<211> LENGTH: 10
```

```
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid

<400> SEQUENCE: 7

Cys Asp Xaa Xaa Glu Xaa Xaa Ser Arg Cys
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 8

Cys Asp Xaa Asp Xaa Xaa Ser Lys Xaa Cys
1               5                   10

<210> SEQ ID NO 9
<211> LENGTH: 5
<212> TYPE: PRT
<213> ORGANISM: Artificial Sequence
<220> FEATURE:
<223> OTHER INFORMATION: Synthetic

<400> SEQUENCE: 9

Tyr Ile Ser Gly Arg
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic

<400> SEQUENCE: 10

Arg Glu Met Ser Asp Trp Arg Val
1               5

<210> SEQ ID NO 11
<211> LENGTH: 6
<212> TYPE: PRT
<213> ORGANISM: Artificial Sequence
<220> FEATURE:
<223> OTHER INFORMATION: Synthetic

<400> SEQUENCE: 11
```

```
Gly Arg Gly Thr Trp Asn
1               5
```

<210> SEQ ID NO 12
<211> LENGTH: 4
<212> TYPE: PRT
<213> ORGANISM: Artificial Sequence
<220> FEATURE:
<223> OTHER INFORMATION: Synthetic

<400> SEQUENCE: 12

```
Gly Gly Tyr Arg
1
```

<210> SEQ ID NO 13
<211> LENGTH: 13
<212> TYPE: PRT
<213> ORGANISM: Artificial Sequence
<220> FEATURE:
<223> OTHER INFORMATION: Synthetic

<400> SEQUENCE: 13

```
Gly Gly Ala Gly Asp Met Trp Glu Arg Val Ser Arg Gly
1               5                   10
```

<210> SEQ ID NO 14
<211> LENGTH: 13
<212> TYPE: PRT
<213> ORGANISM: Artificial Sequence
<220> FEATURE:
<223> OTHER INFORMATION: Synthetic

<400> SEQUENCE: 14

```
Arg Lys Ile Ser Ala Ser Glu Phe Asp Arg Pro Leu Arg
1               5                   10
```

<210> SEQ ID NO 15
<211> LENGTH: 5
<212> TYPE: PRT
<213> ORGANISM: Artificial Sequence
<220> FEATURE:
<223> OTHER INFORMATION: Synthetic

<400> SEQUENCE: 15

```
Gly Trp Ser Tyr Gly
1               5
```

<210> SEQ ID NO 16
<211> LENGTH: 108
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(50)
<223> OTHER INFORMATION: These residues can be any naturally occurring
      amino acid and may be present or absent.
<220> FEATURE:
<221> NAME/KEY: misc_feature
<222> LOCATION: (52)..(53)
<223> OTHER INFORMATION: Xaa can be any naturally occurring amino acid
<220> FEATURE:
<221> NAME/KEY: misc_feature
<222> LOCATION: (55)..(56)
<223> OTHER INFORMATION: Xaa can be any naturally occurring amino acid
<220> FEATURE:
<221> NAME/KEY: MISC_FEATURE
<222> LOCATION: (59)..(108)
<223> OTHER INFORMATION: These residues can be any naturally occurring -continued amino acid and may be present or absent.

<400> SEQUENCE: 16

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Asp Xaa Xaa Glu Xaa Xaa Ser Arg Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
            85                  90                  95

Xaa Xaa Xaa Xaa Xaa Xaa Xaa Xaa Xaa Xaa Xaa Xaa
            100                 105

<210> SEQ ID NO 17
<211> LENGTH: 108
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(50)
<223> OTHER INFORMATION: These residues can be any naturally occurring
      amino acid and may be present or absent.
<220> FEATURE:
<221> NAME/KEY: misc_feature
<222> LOCATION: (52)..(52)
<223> OTHER INFORMATION: Xaa can be any naturally occurring amino acid
<220> FEATURE:
<221> NAME/KEY: misc_feature
<222> LOCATION: (54)..(55)
<223> OTHER INFORMATION: Xaa can be any naturally occurring amino acid
<220> FEATURE:
<221> NAME/KEY: misc_feature
<222> LOCATION: (58)..(58)
<223> OTHER INFORMATION: Xaa can be any naturally occurring amino acid
<220> FEATURE:
<221> NAME/KEY: MISC_FEATURE
<222> LOCATION: (59)..(108)
<223> OTHER INFORMATION: These residues can be any naturally occurring
      amino acid and may be present or absent.

<400> SEQUENCE: 17

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Asp Xaa Asp Xaa Xaa Ser Lys Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
            85                  90                  95

Xaa Xaa Xaa Xaa Xaa Xaa Xaa Xaa Xaa Xaa Xaa Xaa
            100                 105